US007956046B2

(12) United States Patent
Laux et al.

(10) Patent No.: US 7,956,046 B2
(45) Date of Patent: Jun. 7, 2011

(54) OLIGOSACCHARIDE MIXTURES DERIVED FROM HEPARIN, PREPARATION THEREOF AND PHARMACEUTICAL COMPOSITIONS CONTAINING THEM

(75) Inventors: Volker Laux, Mainz (DE); Pierre Mourier, Charenton la Pont (FR); Christian Viskov, Ris Orangis (FR)

(73) Assignee: Aventis Pharma S.A., Antony Cedex (FR)

( * ) Notice: Subject to any disclaimer, the term of this patent is extended or adjusted under 35 U.S.C. 154(b) by 608 days.

(21) Appl. No.: 10/899,618

(22) Filed: Jul. 27, 2004

(65) Prior Publication Data
US 2005/0090561 A1   Apr. 28, 2005

Related U.S. Application Data

(63) Continuation-in-part of application No. PCT/FR2004/001943, filed on Jul. 22, 2004.

(60) Provisional application No. 60/516,926, filed on Nov. 3, 2003.

(30) Foreign Application Priority Data

Jul. 24, 2003   (FR) ...................... 03 09041

(51) Int. Cl.
*A61K 31/715*   (2006.01)
*C07H 1/00*   (2006.01)
(52) U.S. Cl. ...................... 514/54; 536/123.1
(58) Field of Classification Search .............. 514/54; 536/123.1
See application file for complete search history.

(56) References Cited

U.S. PATENT DOCUMENTS

| 4,168,377 A | 9/1979 | Choay et al. |
| 4,401,662 A | 8/1983 | Lormeau et al. |
| 4,401,758 A | 8/1983 | Lormeau et al. |
| 4,440,926 A | 4/1984 | Mardiguian |
| 4,474,770 A | 10/1984 | Lormeau et al. |
| 4,500,519 A | 2/1985 | Lormeau et al. |
| 4,533,549 A | 8/1985 | Lasker |
| 4,686,288 A | 8/1987 | Lormeau et al. |
| 4,826,827 A | 5/1989 | Lormeau et al. |
| 4,981,955 A | 1/1991 | Lopez |
| 4,987,222 A | 1/1991 | DeAmbrosi et al. |
| 5,380,716 A | 1/1995 | Conrad et al. |
| 5,389,618 A | 2/1995 | Debrie |
| 5,576,304 A | 11/1996 | Kakkar et al. |
| RE35,770 E | 4/1998 | Lormeau et al. |
| 6,001,820 A | 12/1999 | Hirsh et al. |
| 6,075,013 A | 6/2000 | Weitz et al. |
| 6,103,705 A | 8/2000 | Uzan et al. |
| 6,197,943 B1 | 3/2001 | Casu et al. |
| 6,384,021 B1 | 5/2002 | Mardiguian |
| 6,617,316 B1 * | 9/2003 | Mourier et al. ............... 514/56 |
| RE38,743 E | 6/2005 | Debrie |
| 6,969,705 B2 | 11/2005 | Pecquet et al. |
| 2002/0055621 A1 | 5/2002 | Diaz et al. |
| 2004/0171819 A1 | 9/2004 | Viskov |
| 2005/0171055 A1 | 8/2005 | Pecquet et al. |
| 2008/0182820 A1 | 7/2008 | Viskov |

FOREIGN PATENT DOCUMENTS

| AU | B-70519/81 | 11/1981 |
| EP | 0 027 089 A1 | 4/1981 |
| EP | 0 037 319 A1 | 10/1981 |
| EP | 0 040 144 A1 | 11/1981 |
| EP | 0 114 589 A1 | 8/1984 |
| EP | 0 293 539 A2 | 12/1988 |
| EP | 1 070 503 A1 | 1/2001 |
| ES | 2 077 533 A1 | 11/1995 |
| FR | 2 663 639 A1 | 12/1991 |
| FR | 2811992 A1 * | 1/2002 |
| WO | WO 81 02737 A1 | 10/1981 |
| WO | WO 98/55515 | 12/1998 |
| WO | WO 0129055 A2 * | 4/2001 |
| WO | WO 02/08295 A1 | 1/2002 |

OTHER PUBLICATIONS

Galezowski, W. et al., "Homoconjugated Hydrogen Bonds with Amidine and Guanidine Bases, Osmometric, Potentiometric and FTIR Studies," J. Chem. Soc., Faraday Transactions, 93(15), pp. 2515-2518, 1997.
International Search Report mailed Dec. 6, 2001, for PCT Application No. PCT/FR01/02332, filed Jul. 18, 2001 (4 pages).
Schwesinger, R. et al., "Peralkylated Polyaminophosphazenes—Extremely Strong, Neutral Nitrogen Bases," Angew. Chem. Int. Ed. Engl., 26(11), pp. 1167-1169, 1987.
Schwesinger, R., et al., "How Strong and How Hindered Can Uncharged Phosphazene Bases Be?" Angew. Chem. Int. Ed. Engl., 32, No. 9, pp. 1361-1363, 1993.
Ungria, Javier, European Patent Office letter, Re: European Patent Application No. 01955436.9 (Publication No. EP-1307491) in the name of Aventis Pharma, S.A., pp. 1-4, Jul. 30, 2004. Vila, P. et al., "Preparation of Saccharide Oligomers by Chemical Depolymerization of Heparin Derivatives," Chemical Abstracts Service, Database Accession No. 125:303695 w, pp. 163-164, Dec. 9, 1996.
Office Action dated May 5, 2008, in U.S. Appl. No. 11/096,146.
English language Derwent abstract of EP 0 040 144 A1, Nov. 18, 1981.
English language Derwent abstract of EP 0 037 319 A1, Oct. 7, 1981.
English language Derwent abstract of FR 2 663 639 A1, Dec. 27, 1991.
English language Derwent abstract of EP 0 027 089 A1, Apr. 15, 1981.

(Continued)

*Primary Examiner* — Shaojia Anna Jiang
*Assistant Examiner* — Everett White
(74) *Attorney, Agent, or Firm* — McCarter & English, LLP

(57) ABSTRACT

Oligosaccharide mixtures comprising anti-Xa activities of from 190 IU/mg to 450 IU/mg and anti-IIa activities of less than 0.2 IU/mg; and having constituent oligosaccharides with an average molecular weight of from 1800 to 2400 Daltons, constituent oligosaccharides comprise from 2 to 16 saccharide units, a 4,5-unsaturated uronic acid 2-O-sulfate unit at one end, and comprising at least one ΔIIa-IIs-Is hexasaccharide sequence are described. Processes for preparing the oligosaccharide mixtures, pharmaceutical compositions and articles of manufacture comprising the oligosaccharide mixtures are described. Methods of treatment and prevention comprising administering the oligosaccharide mixtures are described.

16 Claims, No Drawings

OTHER PUBLICATIONS

English language Derwent abstract of ES 2 077 533 A1, Nov. 16, 1995.
English language Derwent abstract of WO 81 02737 A1, Oct. 1, 1981.
English language Derwent abstract of EP 0 293 539 A2, Dec. 7, 1988.
Barrowcliffe et al., "Anticoagulant Activities of Lung and Mucous Heparins," Thromb. Res., 12(1): 27-36 (1977).
Barrowcliffe et al., "Standardization of Low Molecular Weight Heparins: A Collaborative Study," Thrombosis and Haemostasis, 54(3): 675-679 (1985).
Barrowcliffe et al., "An International Standard for Low Molecular Weight Heparin," Thrombosis and Haemostasis, 60(1): 1-7 (1988).
Choay et al., "Structural Studies on a Biologically Active Hexasaccharide Obtained from Heparin," Annals of the New York Academy of Sciences, 370: 644-649 (1981).
Hook et al., "Anticoagulant Activity of Heparin: Separation of High-Activity and Low-Activity Heparin Species by Affinity Chromatography on Immobilized Antithrombin," F.E.B.S. Letters, 66(1): 90-93 (1976).
Lane et al., "Anticoagulant Activities of Four Unfractionated and Fractionated Heparins," Thromb. Res., 12(2): 257-271 (1978).
Teien et al., "Evaluation of a Amidolytic Heparin Assay Method: Increased Sensitivity by Adding Purified Antithrombin III," Thromb. Res., 10(3): 399-410 (1977).
Andersson et al., "Molecular Weight Dependency of the Heparin Potentiated Inhibition of Thrombin and Activated Factor X, Effect of Heparin Neutralization in Plasma," Thromb. Res., 15(3/4): 531-541 (1979).
Declaration Pursuant to 37 C.F.R. § 1.132 of Dr. Christian Viskov, dated Nov. 26, 2003, for U.S. Appl. No. 10/430,435, filed May 7, 2003, including attached Tables 1(a), 1(b), and 2 (8 pages total).
Office Action dated Jul. 30, 2002 in U.S. Appl. No. 09/090,797.
Office Action dated Mar. 11, 2003 in U.S. Appl. No. 09/909,797.
Office Action dated Jul. 14, 2003 in U.S. Appl. No. 09/909,797.
Office Action dated May 17, 2004 in U.S. Appl. No. 09/909,797.
Office Action dated Jan. 21, 2005 in U.S. Appl. No. 09/909,797.
Office Action dated Aug. 9, 2006 in U.S. Appl. No. 10/680,934.
Office Action dated Apr. 19, 2006 in U.S. Appl. No. 10/680,934.
Office Action dated Mar. 31, 2006 in U.S. Appl. No. 11/096,146.
Office Action dated Nov. 22, 2006 in U.S. Appl. No. 11/096,146.
Office Action dated Aug. 6, 2007 in U.S. Appl. No. 11/096,146.

\* cited by examiner

OLIGOSACCHARIDE MIXTURES DERIVED FROM HEPARIN, PREPARATION THEREOF AND PHARMACEUTICAL COMPOSITIONS CONTAINING THEM

This application claims the benefit of U.S. Provisional Patent Application No. 60/516,926, filed Nov. 3, 2003. This application is also a continuation-in-part of PCT Application No. PCT/FR04/01943, filed Jul. 22, 2004, which claims the benefit of French Patent Application No. 0309041, filed Jul. 24, 2003.

Heparin is a mixture of sulfated mucopolysaccharides of animal origin, such as porcine or bovine. Heparin has been used medically for its anticoagulant and antithrombotic properties. However, the significant anticoagulant (anti-IIa) activity of heparin can cause hemorrhages, restricting the conditions of its use.

Low molecular weight heparins obtained by alkaline depolymerization of heparin esters have been proposed as alternatives to heparin. The physical and chemical characteristics of heparins and low molecular weight heparins, as well as the resulting biological activities of these molecules, are related to the preparation process used. More recently, low molecular weight heparins have been described.

As used in the present specification, the following words and phrases are generally intended to have the meanings as set forth below, except to the extent that the context in which they are used indicates otherwise.

As used herein, the term "depolymerization" (and variations thereof such as depolymerize or depolymerizing) includes all types of depolymerization, including without limitation fragmentation, chemical or enzymatic depolymerization, and other methods of preparing fragments of heparin, including without limitation, fractionation.

As used herein, the term "low molecular weight heparin" or "LMWH" means a mixture of polysaccharides obtained from heparin and having a weight average molecular weight of greater than approximately 1,500 Daltons and less than approximately 10,000 Daltons. In some embodiments, the low molecular weight heparin is a mixture of polysaccharides obtained from heparin and having a weight average molecular weight of greater than approximately 1,500 Daltons and less than approximately 4,000 Daltons.

The "mean molecular weight", "average molecular weight", "number average molecular weight", and "weight average molecular weight" of compositions of the invention can be determined by high-pressure liquid chromatography. An example of this method uses two columns in series, for example those marketed by Tosoh Bioscience, Montgomeryville, Pa., under the name TSK G3000 XL and TSK G2000 XL. The detection may be performed by refractometry, using a lithium nitrate eluent and a flow rate of 0.6 ml/minute. The system may be calibrated with standards prepared by fractionation of Enoxaparin by chromatography on agarose-polyacrylamide gel (IBF). This preparation may be performed according to the technique described by Barrowcliffe et al, Thromb. Res., 12, 27-36 (1977-78) or D. A. Lane et al, Thromb. Res., 12, 257-271 (1977-78). The results can be calculated with the GPC6 software (Perkin Elmer).

As used herein, "anti-Xa activity is a rough measure of antithrombotic effect and is evaluated in vitro through an assay of specific factor X activated inhibition. Anti-Xa activity may be measured, for example, via the amidolytic method on a chromogenic substrate according to the principle described by Teien et al, Thromb. Res., 10, 399-410 (1977). The assays may be performed according to the method described in the monograph on low molecular weight heparins of the European pharmacopea in force, with the exception that the reconstitution buffer may be modified by replacing the albumin in the tris-NaCl buffer, pH 7.4, with polyethylene glycol 6000(PEG 6000). The anti Xa activity may be measured relative to a standard low molecular weight heparin (which measures from 140 to 180 U/mg (dry weight)). Anti-Xa activity may alternatively be measured, for example, by the method described in Barrowcliffe, T. W., A. D. Curtis, et al. (1985). "Standardization of Low Molecular Weight Heparins: A Collaborative Study." Thrombosis and Haemostasis 54: 675-679. See, also, Barrowcliffe, T. W. (1988). "An International Standard for Low Molecular Weight Heparin." Thrombosis and Haemostasis 60: 1-7. Anti-Xa activity measured in vitro is, however, not to be confused with antithrombotic effect or activity, which relates to a complicated in vivo process. For example, the specification of U.S. Pat. No. 5,389,618 discloses that the LMWHs reported therein have a better antithrombotic activity greater than heparin and supports that assertion by providing pharmacological evidence showing that, relative to heparin, the LMWHs disclosed therein better prevent venous thromboses in "patient risk situations," and that those mixtures are "useful therapeutic compositions" whose "administration . . . provides . . . a decrease in the risks [from approximately 25% with heparin to only about 10% with the admixtures of the invention] of acute thrombotic events attendant orthopedic surgery." Col. 6:24-33 (emphasis added).)

The activity of the standard LMWH may be measured relative to the first international low molecular weight heparin standard. This standard LMWH was prepared according to the teaching of patent applications of WO 02/08295 and WO 2004/033503. The activity of the standard LMWH is measured relative to the international low molecular weight heparin standard.

As used herein, "anti-IIa activity" is a measure of anticoagulant effect and can be evaluated in vitro through an assay of inhibitory effect against human thrombin (IIa). The anti-IIa activity may be measured by the technique described by Anderson L. O. et al., Thromb. Res., 15, 531-541 (1979), with, as standard, the first international standard for low-molecular-weight heparins. Anti-IIa activity may alternatively be measured, for example, via the amidolytic method on a chromogenic substrate according, for example, to the method described in the monograph on low molecular weight heparins of the European pharmacopea in force. The anti-IIa activity may be measured relative to a standard Low Molecular Weight Heparin (LMWH) having a measured activity of 2.1 IU/mg. The activity of the standard LMWH is measured relative to the international low molecular weight heparin standard.

As used herein, "degree of esterification" or "esterification degree" refers to the amount of benzyl alcohol (in grams) produced by saponification of a heparin benzyl ester (typically at 0° C.) divided by the amount of the heparin benzyl ester and is generally expressed as a percentage, as explained in U.S. Pat. No. 5,389,618, col. 5, lines 40-48 and Examples 3 and 5.

As used herein, "esterification percentage" or "percent esterification" refers to the quantity (in moles) of carboxylate functionality after esterification divided by the quantity (in moles) of initial carboxylate functionality and is generally expressed as a percentage. Quantity of carboxylate functionality can be determined, for example, by potentiometric titration with a strong acid.

As used herein, with regard to assessing degree of esterification or percent esterification, the term "purified" (and variations thereof such as purify or purification) means, as is well-known, sufficiently homogeneous to appear free of readily detectable impurities, such as salts, for example, quaternary ammonium salts or sodium chloride; benzyl derivatives, for example, benzyl alcohol, benzyl chloride, and benzyl ether; non-heparin esters; and the like, as determined by standard methods of analysis, such as high performance liquid chromatography (HPLC), used by those of skill in the art to assess such purity. The degree of purity may be determined by, for example, steric exclusion liquid chromatography.

The percentage of the hexasaccharide fraction present in an oligosaccharide mixture of the invention may be determined analytically, for example, by high-pressure liquid chromatography on TSK G3000 XL and TSK G2000 XL columns (available from by Tosoh Bioscience, Montgomeryville, Pa.) or by preparative separation of the hexasaccharide fraction by any suitable method. For example, the mixture may be chromatographed on columns filled with gel of polyacrylamide agarose type. The mixture can be eluted with aqueous base, such as an aqueous sodium hydrogen carbonate solution, such as a sodium hydrogen carbonate solution of from 0.1 mol/l to 1 mol/l. The detection may be performed by UV spectrometry (254 nm). After fractionation, the hexasaccharide fraction in solution may be neutralized with an acid, such as acetic acid, for example, glacial acetic acid. The solution may then be concentrated under reduced pressure. In certain embodiments when the hexasaccharide fraction is eluted with aqueous sodium hydrogen carbonate and then neutralized with acetic acid, the solution is concentrated so as to obtain a sodium acetate concentration of, for example, greater than 30% by weight. The hexasaccharide fraction may be precipitated by addition of an excess of a polar, protic solvent such as 3 to 5 volumes of methanol. The hexasaccharide fraction can then be recovered, for example, by filtration through a No. 3 sinter funnel. The hexasaccharide mixture obtained may be analyzed by high performance liquid chromatography (HPLC) to determine its content of hexasaccharide ΔIIa-IIs-Is. The hexasaccharide ΔIIa-IIs-Is may be isolated by preparative HPLC or by affinity chromatography on an antithrombin III sepharose column according to the techniques used by those skilled in the art, such as that described in M. Hook, et al, F.E.B.S letters, Vol 656(1) (1976).

As used herein, the term "prevent," "preventing" or "prevention" refers to the administration of therapy on a prophylactic or preventative basis to an individual who may ultimately manifest at least one symptom of a disease or condition (e.g., thrombosis) but who has not yet done so. Such individuals may be identified on the basis of risk factors that are known to correlate with the subsequent occurrence of the disease. Alternatively, prevention therapy may be administered without prior identification of a risk factor, as a prophylactic measure. Delaying the onset of the at least one symptom may also be considered prevention or prophylaxis.

As used herein, the term "treat," "treating" or "treatment" refers to the administration of therapy to an individual who already manifests at least one symptom of a disease or condition (e.g., thrombosis), or who has previously manifested at least one symptom of a disease or condition.

As used herein, "pharmaceutically acceptable carrier" refers to a non-toxic solid, semisolid or liquid filler, diluent, encapsulating material or formulation auxiliary of any conventional type, for example. A "pharmaceutically acceptable carrier" is non-toxic to recipients at the dosages and concentrations employed and is compatible with other ingredients of the formulation. Suitable carriers include, but are not limited to, water, dextrose, glycerol, saline, ethanol, and combinations thereof. The carrier may contain additional agents such as wetting or emulsifying agents, pH buffering agents, or adjuvants which enhance the effectiveness of the formulation. Percutaneous penetration enhancers may also be included. Compositions for oral administration may form solutions, suspensions, tablets, pills, capsules, sustained release formulations or powders.

As used herein, "solution" refers to a homogeneous mixture of two or more substances.

As used herein, "suspension" is a heterogeneous mixture of fine particles of a solid within a liquid, the particles being the dispersed phase, while the suspending medium is the continuous phase.

In an aspect, the invention provides an oligosaccharide mixture, wherein:
the oligosaccharide mixture comprises an anti-Xa activity of from 190 IU/mg to 450 IU/mg;
the oligosaccharide mixture comprises an anti-IIa activity of less than 0.2 IU/mg;
the constituent oligosaccharides of the mixture have an average molecular weight of from 1800 to 2400 Daltons;
the constituent oligosaccharides of the mixture comprise from 2 to 16 saccharide units;
the constituent oligosaccharides of the mixture have a 4,5-unsaturated uronic acid 2-O-sulfate unit at one end; and
the constituent oligosaccharides of the mixture comprise oligosaccharides comprising a hexasaccharide of the following formula:

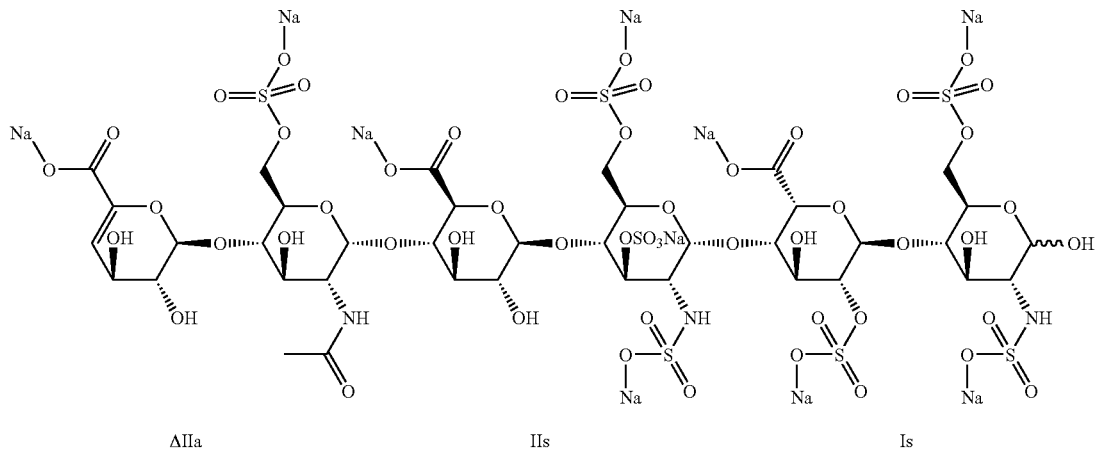

wherein the constituent oligosaccharides of the mixture are in the form of at least one metal salt chosen from alkali metal and alkaline-earth metal salts.

In an aspect, the invention provides an oligosaccharide mixture, wherein:

the mixture comprises an anti-Xa activity of from 190 IU/mg to 450 IU/mg;

the mixture comprises an anti-IIa activity of less than 0.2 IU/mg;

the constituent oligosaccharides of the mixture have an average molecular weight of from 1800 to 2400 Daltons;

the constituent oligosaccharides of the mixture comprise from 2 to 16 saccharide units; and the constituent oligosaccharides of the mixture have a 4,5-unsaturated uronic acid 2-O-sulfate unit at one end;

wherein:

from 20% to 100% of the oligosaccharides of the mixture are hexasaccharides;

from 20% to 70% of the hexasaccharides have the sequence:

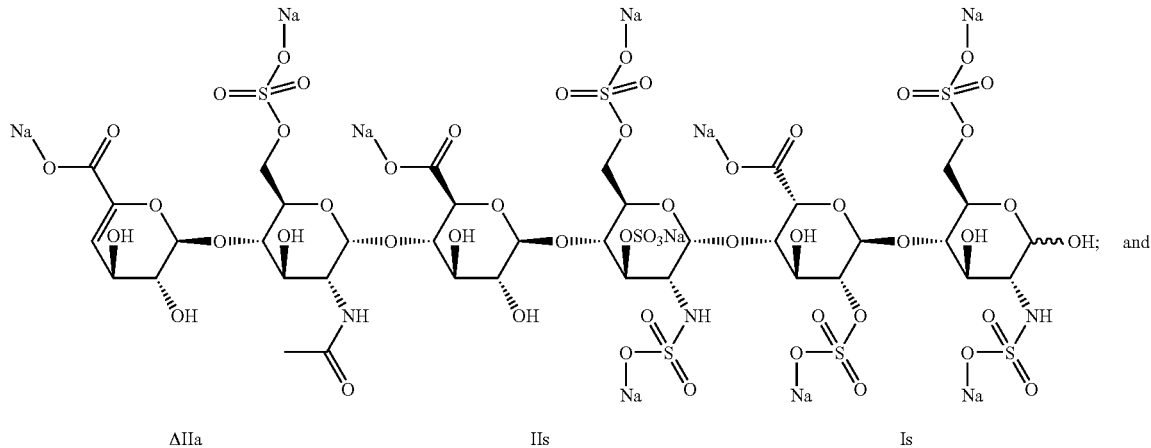

ΔIIa           IIs           Is the constituent oligosaccharides of the mixture are in the form of at least one metal salt chosen from alkali metal and alkaline-earth metal salts.

In certain embodiments, the mixture comprises an anti-Xa activity of from 190 IU/mg to 410 IU/mg. In certain embodiments, the mixture comprises an anti-Xa activity of from 200 IU/mg to 300 IU/mg. In certain embodiments, the constituent oligosaccharides of the mixture have an average molecular weight of from 1900 to 2200 Daltons. In certain embodiments, the constituent oligosaccharides of the mixture have an average molecular weight of from 1950 to 2150 Daltons. In certain embodiments, the constituent oligosaccharides of the mixture have an average molecular weight of 2000 Daltons.

In certain embodiments, 20% to 100% (and in some embodiments, from 20% to 70%) of the oligosaccharides of the mixture are hexasaccharides. In certain embodiments, from 20% to 70% (and in some embodiments, from 25% to 50%) of the hexasaccharide fraction of the oligosaccharide mixture has the sequence:

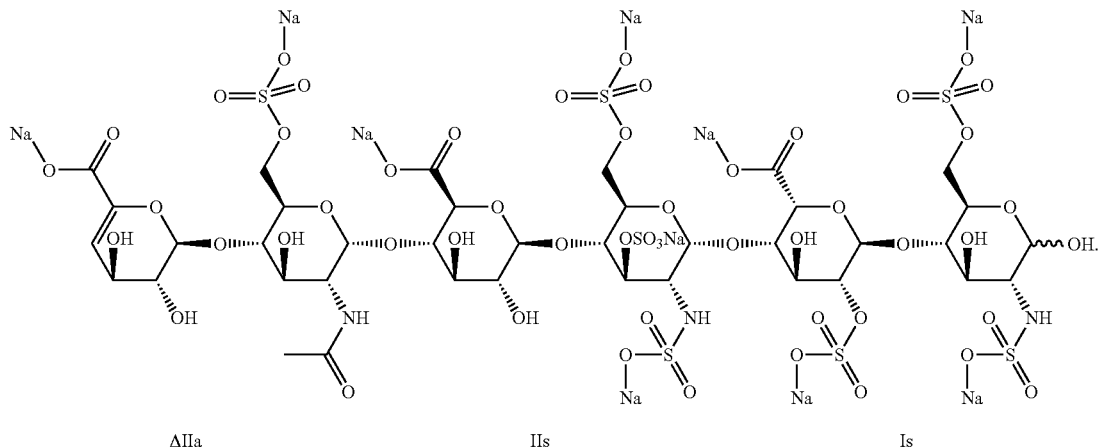

ΔIIa           IIs           Is

In certain embodiments, the alkali metal or alkaline-earth metal salts are one or more of sodium, potassium, calcium and magnesium salts. In certain embodiments, the alkali metal or alkaline-earth metal salt is a sodium salt.

In an aspect, the invention provides a process for preparing an oligosaccharide mixture, comprising:

providing a quaternary ammonium salt of a low molecular weight heparin benzyl ester having an anti-IIa activity of from 0.2 to less than 5 IU/mg and an average molecular weight of from 1500 to 4,000 Daltons; and depolymerization said quaternary ammonium salt of a low molecular weight heparin benzyl ester by means of a strong organic base with a pKa value of greater than 20, so as to obtain a depolymerized low molecular weight heparin.

In certain embodiments, the process further comprises the step of converting the quaternary ammonium salt of the depolymerized low molecular weight heparin into at least one metal salt chosen from alkali metal and alkaline-earth metal salts. In certain embodiments, after the quarternary ammonium salt is converted into at least one metal salt chosen from alkali metal and alkaline-earth metal salts, the process further comprises the step of saponifying any residual esters. In certain embodiments, after the residual esters are saponified, said process further comprises the step of removing disaccharide and tetrasaccharide fractions.

In certain embodiments, the quaternary ammonium salt of a low molecular weight heparin benzyl ester is prepared by providing a low molecular weight benzethonium heparinate;

esterifying said benzethonium heparinate to obtain a sodium salt; and transsalifiying the sodium salt to produce a quaternary ammonium salt.

In certain embodiments, the depolymerization is performed with a molar ratio of strong organic base to benzyl ester of the LMWH of from about 0.2:1 to about 5:1 and in some embodiments, from about 0.6:1 to about 2:1.

In some embodiments, the strong organic base has the formula:

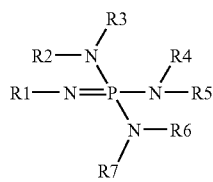

in which the radicals $R_1$ to $R_7$, which are identical or different, are chosen from linear, branched and cyclic alkyl radicals, it being possible for $R_3$ and $R_4$, where appropriate, to form, with the —N—P—N group which carries them, a 6-membered heterocycle. In some embodiments, the strong organic base is tert-Octylimino-tris(dimethylamino)phosphorane, 2-tert-Butylimino-2-diethylamino-1,3-dimethyl-perhydro-1,3,2-diazaphosphorine, N'-tert-Butyl-N,N,N',N',N",N"-hexamethylphosphorimidic triamide, or tert-Butylimino-tri(pyrrolidino)phosphorane, or 2-tert-Butylimino-2-diethylamino-1,3-dimethyl-perhydro-1,3,2-diazaphosphorine on polystyrene. In some embodiments, the strong organic base is 2-tert-butylimino-2-diethylamino-1,3-dimethylperhydro-1,3,2-diazaphosphorine.

In some embodiments, the conversion of the quaternary ammonium salt of the benzyl ester of the LMWH into the sodium salt comprises treating the quaternary ammonium salt with alcoholic sodium acetate solution. In some embodiments, the quaternary ammonium salt of the benzyl ester of the LMWH is a benzethonium, cetylpyridinium or cetyltrimethylammonium salt.

In some embodiments, the step of saponifying comprises using an alkali metal hydroxide, in aqueous medium, at a temperature of from about 0° C. to about 20° C. In some embodiments, the alkali metal hydroxide is selected from sodium hydroxide, potassium hydroxide and lithium hydroxide.

In an aspect, the invention provides a process for preparing an oligosaccharide mixture, comprising:

providing a LMWH having an anti-IIa activity of from 0.2 to less than 5 IU/mg, and an average molecular weight of from 1,500 Daltons to 4,000 Daltons; and subjecting the LMWH to the following chemical reactions:

a) transsalification by the action of benzethonium chloride to obtain benzethonium heparinate;

b) esterification of the benzethonium heparinate, and treatment to obtain a sodium salt of the benzyl ester of the LMWH;

c) transsalification of the sodium salt of the benzyl ester and production of a quaternary ammonium salt;

d) depolymerization by means of a strong organic base, so as to obtain a depolymerized LMWH;

e) conversion of the quaternary ammonium salt of the depolymerized low molecular weight heparin into at least one metal salt chosen from alkali metal and alkaline-earth metal salts salt; and f) saponification of the residual esters and optional purification;

wherein:

the oligosaccharide mixture comprises an anti-Xa activity of from 190 IU/mg to 450 IU/mg;

the oligosaccharide mixture comprises an anti-IIa activity of less than 0.2 IU/mg;

the constituent oligosaccharides of the mixture have an average molecular weight of from 1800 to 2400 Daltons;

the constituent oligosaccharides of the mixture comprise from 2 to 16 saccharide units;

the constituent oligosaccharides of the mixture have a 4,5-unsaturated uronic acid 2-O-sulfate unit at one end; and the constituent oligosaccharides of the mixture comprise oligosaccharides comprising a hexasaccharide of the following formula:

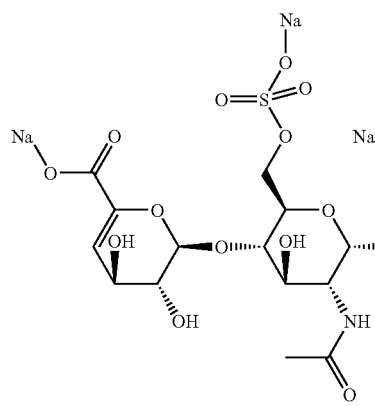
ΔIIa

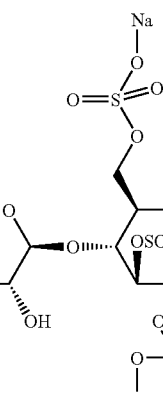
IIs

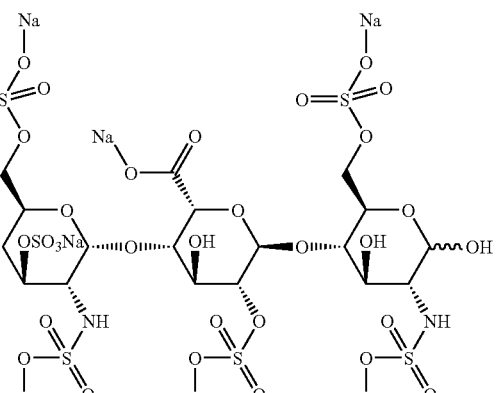
Is wherein the constituent oligosaccharides of the mixture are in the form of at least one metal salt chosen from alkali metal and alkaline-earth metal salts.

In an aspect, the invention provides an oligosaccharide mixture prepared by a process described herein.

In an aspect, the invention provides a pharmaceutical composition comprising an oligosaccharide mixture and a pharmaceutically acceptable carrier. The composition may be formulated as a solution for subcutaneous or intravenous injection; for pulmonary inhalation; or for oral administration.

The invention also provides methods of treating and/or preventing one or more of venous thrombosis, arterial thrombosis, deep vein thrombosis, pulmonary embolism, unstable angina, myocardial infarction, cardiac ischemia, occlusive diseases of the peripheral arteries and atrial fibrillation, smooth muscle cell proliferation, atherosclerosis, arteriosclerosis, cancer by modulating angiogenesis and growth factors, and also diabetic disorders such as diabetic retinopathy or diabetic nephropathy in a patient, the method comprising administering to a patient in need thereof a therapeutically effective amount of the oligosaccharide mixture described herein. Also provided are methods for preventing thrombotic episodes in a patient, comprising administering to a patient in need thereof a therapeutically effective amount of the oligosaccharide mixture; methods for treating thrombotic episodes in a patient, comprising administering to a patient in need thereof a therapeutically effective amount of the oligosaccharide mixture; methods for preventing venous thrombosis is a postoperative human patient, comprising administering to a patient in need thereof a therapeutically effective amount of the oligosaccharide mixture; methods for treating venous thrombosis is a postoperative human patient, comprising administering to a patient in need thereof a therapeutically effective amount of the oligosaccharide mixture; and therapeutic methods for controlling thrombosis and/or decreasing blood hypercoagulation and/or hemorrhaging risks in a human patient, comprising administering to a patient in need thereof a therapeutically effective amount of the oligosaccharide mixture.

The invention further provides articles of manufacture for use in connection with the treatment and/or prevention of venous thrombosis, arterial thrombosis, deep vein thrombosis, pulmonary embolism, unstable angina, myocardial infarction, cardiac ischemia, occlusive diseases of the peripheral arteries and atrial fibrillation, smooth muscle cell proliferation, atherosclerosis, arteriosclerosis, cancer by modulating angiogenesis and growth factors, and also diabetic disorders such as diabetic retinopathy or diabetic nephropathy in a patient, comprising the oligosaccharide mixture and instructions for the administration thereof; articles of manufacture for use in connection with the prevention of thrombotic episodes in a patient, comprising the oligosaccharide mixture and instructions for the administration thereof; articles of manufacture for use in connection with the treatment of thrombotic episodes in a patient, comprising the oligosaccharide mixture and instructions for the administration thereof; articles of manufacture for use in connection with the prevention of venous thrombosis is a postoperative human patient, comprising the oligosaccharide mixture and instructions for the administration thereof; articles of manufacture for use in connection with the treatment of venous thrombosis is a postoperative human patient, comprising the oligosaccharide mixture and instructions for the administration thereof; articles of manufacture for use in connection with controlling thrombosis and/or decreasing blood hypercoagulation and/or hemorrhaging risks in a human patient, comprising the oligosaccharide mixture and instructions for the administration thereof.

The invention also provides methods for determining the anti-Xa activity of the oligosaccharide mixture wherein an amidolytic method is used on a chromogenic substrate in which the reconstitution buffer is Polyethylene Glycol 6000 (PEG 6000).

The oligosaccharide mixtures according to the invention are prepared by depolymerization of a quaternary ammonium salt of the benzyl ester of a low molecular weight heparin (LMWH) in organic medium, this LMWH being prepared according to the teaching of patent applications WO 02/08295 and WO 2004/033503, each of which is incorporated herein by reference for all purposes to the extent they describe methods of preparing LMWHs. In some embodiments, the depolymerization of the low molecular weight heparin is conducted in the presence of a strong base, in an inert solvent, and in the presence of a percentage of water of less than 3%.

In some embodiments, the LMWHs used as starting material have anti-IIa activity of from 0.2 to less than 5 IU/mg and average molecular weight of from 1500 to 4000 Daltons. In some embodiments, the LMWH starting material has a molecular weight of from 2000 to 4000 Daltons or from 1500 to 3000 Daltons.

In some embodiments, the LMWH starting material has an anti-Xa activity of greater than 140 IU/mg.

In some embodiments, the LMWH starting material has an anti-Xa activity of less than 140 IU/mg. In some embodiments, the LMWH starting material has an anti-Xa activity of from 100 to 140 IU/mg. See, for example, U.S. Pat. No. 6,384,021 or WO 02/08295.

In some embodiments, the LMWH starting material is, for example, Enoxaparin, Fraxiparin, Fragmin, Innohep (or Logiparin), Normiflo, Embolex (or Sandoparin), Fluxum (or Minidalton), Clivarin and Hibor, all of which are commercially available and all of which are themselves obtained from an unfractionated starting material.

In some embodiments, heparin is used as the starting material in the process described herein to yield a LMWH and the process is then repeated using such LMWH as the starting material. In certain embodiments, heparin is pretreated by treatment with potassium permanganate. For example, heparin is treated with at least one permanganate salt chosen from potassium permanganate, sodium permanganate, and quarternary ammonium permanganate, such as potassium permanganate. In certain embodiments, between about 4% to about 10% by weight relative to the hepain of said permanganate salt is used. In certain embodiments, between about 4% to about 8% of the permanganate salt is used. In certain embodiments, between about 4% and about 8% of potassium permanganate is used.

In some embodiments, the LMWHs used as starting material are prepared by a method comprising:
transsalification of a low molecular weight heparin with anti-IIa activity of from 0.2 to less than 5 IU/mg and an average molecular weight of more than 1500 (or in some embodiments, from 1500 to 10,000 Daltons) by the action of benzethonium chloride to obtain benzethonium heparinate,
esterification of the benzethonium heparinate obtained by the action of benzyl chloride, and treatment with alcoholic sodium acetate solution to obtain a sodium salt of the benzyl ester of the low molecular weight heparin, and
transsalification of the benzyl ester obtained and production of the quaternary ammonium salt, such as the benzethonium, cetylpyridinium or cetyltrimethylammonium salt, to obtain a LMWH having an anti-IIa activity of from 0.2 to less than 5 IU/mg and an average molecular weight of from 1,500 Daltons to 4,000 Daltons (or in some embodiments, from 2000 Daltons to 4000 Daltons; or in some embodiments, from 1500 Daltons to 3000 Daltons.)

In some embodiments, the transsalification of a low molecular weight heparin is performed using a quaternary ammonium chloride, such as benzethonium chloride, cetylpyridinium chloride or cetyltrimethylammonium chloride, in aqueous medium, at a temperature of from about 15 to about 25° C. In some embodiments, the salt/sodium heparin mole ratio is from about 2.5:1 to about 3.5:1.

In some embodiments, the esterification of the benzethonium heparinate is performed in an organic chlorinated solvent (such as chloroform or dichloromethane), at a temperature of from about 25° C. to about 45° C. and, in some embodiments, from about 30° C. to about 40° C. The ester in the form of the sodium salt is then recovered by precipitation using 10% by weight of sodium acetate in an alcohol such as methanol. 1 to 1.2 volumes of alcohol per volume of reaction medium are generally used. In some embodiments, the amount of benzyl chloride and the reaction time are adapted to obtain a percent esterification of from 40% to 100%. In some embodiments, the amount of benzyl chloride and the reaction time are adapted to obtain a percent esterification of from 70% to 90%. In some embodiments, from 0.5 to 1.5 parts by weight of benzyl chloride per 1 part by weight of the benzethonium salt of heparin are used. In some embodiments, the reaction time will be from 10 to 35 hours.

In some embodiments, the process according to the invention uses a percent of esterification of the quaternary ammonium salt of the benzyl ester of heparin of from 40% to 100%. In some embodiments, the process according to the invention uses a percent of esterification of from 70 to 90%.

In some embodiments, a second transsalification step is performed using a quaternary ammonium chloride, such as benzethonium chloride, cetylpyridinium chloride or cetyltrimethylammonium chloride, in aqueous medium, at a temperature of from about 10° C. to about 25° C. In some embodiments, the quaternary ammonium chloride/sodium salt of the benzyl ester of heparin mole ratio is from about 2.5:1 to about 3.5:1.

The starting LMWHs are depolymerized using a strong organic base. In some embodiments, the strong organic base has a pKa value of greater than 20. In some embodiments, the strong organic base is a phosphazene derived base (available, for example, from Sigma-Aldrich). See, e.g., Paquette, L. A., "Encyclopedia of Reagents for Organic Synthesis", Wiley, 1995, Vol. 6, 4110., Schwesinger et al, Angew. Chem. Int. Ed. Engl. 26, 1167-1169 (1987), and R. Schwesinger et al, Angew. Chem. 105, 1420 (1993), each of which is incorporated by reference herein.

In some embodiments, the phosphazene derived base is monomeric such as

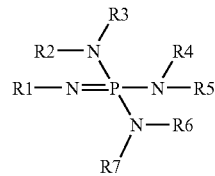

in which the radicals $R_1$ to $R_7$, which are identical or different, are chosen from linear, branched and cyclic alkyl radicals containing from 1 to 6 carbon atoms it being possible for $R_3$ and $R_4$, where appropriate, to form with the —N—P—N— group which carries them, a 6-membered heterocycle. In some embodiments, the phosphazene base is a monomeric base selected from tert-Octylimino-tris(dimethylamino) phosphorane, 2-tert-Butylimino-2-diethylamino-1,3-dimethyl-perhydro-1,3,2-diazaphosphorine, N'-tert-Butyl-N,N,N',N',N'',N''-hexamethylphosphorimidic triamide, tert-Butylimino-tri(pyrrolidino)phosphorane, and 2-tert-Butylimino-2-diethylamino-1,3-dimethyl-perhydro-1,3,2-diazaphosphorine on polystyrene. In some embodiments, the strong organic base is 2-tert-butylimino-2-diethylamino-1,3-dimethylperhydro-1,3,2-diazaphosphorine (official nomenclature: 1,3,2-diazaphosphorin-2-amine, 2[(1,1-dimethylethyl)imino]-N,N-diethyl-1,2,2,2,3,5,6-octahydro-1,3-dimethyl).

In some embodiments, the phosphazene base is a dimeric base selected from 1-tert-Butyl-2,2,4,4,4-pentakis(dimethylamino)-2L5,4L5-catenadi(phosphazene) and 1-Ethyl-2,2,4,4,4-pentakis(dimethylamino)-2L5,4L5-catenadi(phosphazene).

In some embodiments, the phosphazene base is tetrameric base selected from 1-tert-Butyl-4,4,4-tris(dimethylamino)-2,2-bis[tris(dimethylamino)-phosphoranylidenamino]-2Λ⁵,4Λ⁵-catenadi(phosphazene) and 1-tert-Octyl-4,4,4-tris(dimethylamino)-2,2-bis[tris(dimethylamino)
phosphoranylidenamino]-2$\Lambda^5$,4$\Lambda^5$-catenadi(phosphazene).

In some embodiments, the strong base/ester mole ratio is from about 0.2:1 to about 5:1. In some embodiments, the ratio is from about 0.6:1 to about 2:1. In some embodiments, approximately one equivalent of strong organic base is used. In some embodiments, approximately one equivalent of 2-tert-butylimino-2-diethylamino-1,3-dimethylperhydro-1,3,2-diazophosphorine is used.

In some embodiments, the depolymerization is conducted in the presence of less than 3% water. In some embodiments, the depolymerization is conducted under conditions wherein the water content is less than 0.03%. In some embodiments, the water content is less than 0.01%.

In some embodiments, the depolymerization is performed with a molar ratio of strong organic base to benzyl ester of the LMWH of about 1.0:1 and a water content of less than about 0.3%.

In some embodiments, the depolymerization is conducted at a temperature of from about 20° C. to about 40° C. In some embodiments, the depolymerization is conducted at a temperature of from about 20° C. to about 30° C. In some embodiments, the depolymerization is conducted at room temperature. In some embodiments, the depolymerization is conducted at about 30° C.

In some embodiments, the depolymerization is conducted for about 20 to about 40 hours. In some embodiments, the depolymerization is conducted for about 20 to about 30 hours. In some embodiments, the depolymerization is conducted for about 24 hours.

The depolymerization reaction is typically conducted in an inert solvent. In some embodiments, the inert solvent is dichloromethane.

Next, the quaternary ammonium salt of the benzyl ester of the depolymerized LMWH is converted into an alkali metal or alkaline-earth metal salt. In some embodiments, it is converted into a sodium salt. The conversion of the quaternary ammonium salt of the benzyl ester of the depolymerized heparin into the sodium salt may be performed by treating the reaction medium with alcoholic sodium acetate solution, for example, a 10% solution of sodium acetate in methanol (weight/volume), at a temperature of from about 15° C. to about 25° C. In some embodiments, the weight equivalent of acetate added is 3 times as great as the mass of quaternary ammonium salt of the benzyl ester of heparin subsequently used in the depolymerization reaction.

In some embodiments, after the depolymerization, residual esters are saponified using an alkali metal hydroxide selected from sodium hydroxide, potassium hydroxide and lithium hydroxide, in aqueous medium, at a temperature of from about 0° C. to about 20° C. In some embodiments, the temperature is from about 0 to about 10° C. From 1 to 5 molar equivalents of alkali metal hydroxide will generally be used. In some embodiments, the saponification is performed in the presence of from 1 to 2 molar equivalents of alkali metal hydroxide.

The final product may optionally be purified by any known method for purifying depolymerized heparins (for example EP 0 037 319 B1). In some embodiments, the purification is performed using hydrogen peroxide, in aqueous medium, at a temperature of from about 10 to about 50° C. In some embodiments, this operation will be performed at from about 20 to about 40° C.

The mixtures according to the invention in sodium salt form may be converted into at least one metal salt chosen from alkali metal and alkaline-earth metal salts. The conversion from one salt to the other is optionally performed using the method described in patent FR 73/13580.

According to some embodiments of the invention, the selectivity toward factor Xa of the oligosaccharide mixtures may be further increased by removing the disaccharide and tetrasaccharide fractions (fractions not specifically binding to ATIII). In this case, the mixture is chromatographed on a column filled with gel of polyacrylamide agarose type or a polyacrylamide gel. The mixture is eluted with an aqueous base such as sodium hydrogen carbonate solution. In some embodiments, the sodium hydrogen carbonate solution is a solution of from about 0.1 mol/l to about 1 mol/l. In some embodiments, the separation is performed at a concentration of about 1 mol/l. The detection is typically performed by UV spectrometry (at a wavelength of 254 nm).

After removal of the disaccharide and tetrasaccharide fractions, the hexasaccharide fraction is neutralized, for example, by treatment with acetic acid or glacial acetic acid. The solution is then concentrated under reduced pressure. In some embodiments when a sodium hydrogen carbonate solution is used for elution and acetic acid (or glacial acetic acid) is used for naturalization, the reduced solution has a sodium acetate concentration of greater than 30% by weight.

The hexasaccharide fraction is precipitated by addition of a protic, polar solvent such as methanol. In some embodiments, from 3 to 5 volumes of methanol are used. The hexasaccharide fraction is recovered by filtration, for example, using a sinter funnel. Optionally, it may be purified by desalting on a suitable column.

A subject of the invention is thus also a process for preparing the oligosaccharide mixtures as defined above comprising the steps of Depolymerization of a quaternary ammonium salt of a low molecular weight heparin benzyl ester by means of a strong organic base with a pKa value of greater than 20, so as to obtain a depolymerized low molecular weight heparin;

conversion of the quaternary ammonium salt of the depolymerized low molecular weight heparin into at least one metal salt chosen from alkali metal and alkaline-earth metal salts; and saponification of any residual esters. In some embodiments, the saponified product is purified. In some embodiments, the quaternary ammonium salt of the low molecular weight heparin benzyl ester has an anti-IIa activity of from 0.2 to less than 5 IU/mg and an average molecular weight of from 1500 to 4000 Daltons (in some embodiments, from 2000 to 4000 Daltons and in some embodiments, from 1500 to 3000 Daltons). In some embodiments, the process further comprises the step of removing the disaccharide and tetrasaccharide fractions.

In some embodiments, the process for preparing the oligosaccharide mixtures of the invention comprises the steps of:

transsalification of a low molecular weight heparin with anti-IIa activity of from 0.2 to less than 5 IU/mg and an average molecular weight of from 1500 to 4000 Daltons by the action of benzethonium chloride to obtain benzethonium heparinate;

esterification of the benzethonium heparinate obtained by the action of benzyl chloride, and treatment with alcoholic sodium acetate solution to obtain the sodium salt of the benzyl ester of the low molecular weight heparin, transsalification of the benzyl ester obtained and production of the quaternary ammonium salt, such as the benzethonium, cetylpyridinium or cetyltrimethylammonium salt, depolymerization by means of a strong organic base with a pKa value of greater than 20, so as to obtain a depolymerized low molecular weight heparin, conversion of the quaternary ammonium salt of the depolymerized low molecular weight heparin into the sodium salt, and saponification of the residual esters. In some embodiments, the saponified product is purified. In some embodiments, the process further comprises the step of removing the disaccharide and tetrasaccharide fractions.

In some embodiments, the oligosaccharide mixtures have the following characteristics:
an average molecular weight of from 1800 to 2400 Daltons,
anti-Xa activity of from 190 IU/mg to 450 IU/mg,
anti-IIa activity of less than 0.2 IU/mg,
a hexasaccharide fraction of from 20% to 100%; and
20% to 70% of hexasaccharide ΔIIa-IIs-Is in the hexasaccharide fraction.

In some embodiments, the oligosaccharide mixtures have the following characteristics:
the general structure of the constituent polysaccharides of heparin and having the following characteristics:
an average molecular weight of from 1800 to 2400 Daltons,
anti-Xa activity of from 190 IU/mg to 450 IU/mg,
anti-IIa activity of less than 0.2 IU/mg, and
the constituent oligosaccharides of the mixtures comprise from 2 to 16 saccharide units,
have a 4,5-unsaturated uronic acid 2-O-sulfate unit at one of their ends,
comprise oligosaccharides comprising a hexasaccharide of the following formula:

ments, the oligosaccharide mixture has an anti-Xa activity of from 190 to 300 IU.

In some embodiments, the oligosaccharide mixture has an anti-IIa activity of less than 0.2 IU/mg. In some embodiments, the oligosaccharide mixture has an anti-IIa activity that is undetectable using the methods described herein.

According to some embodiments, the oligosaccharide mixture has from 20% to 100% of a hexasaccharide fraction. In some embodiments, this mixture has from 30% to 60% of a hexasaccharide fraction.

According to some embodiments, the oligosaccharide mixture has from 20% to 70% of the hexasaccharide ΔIIa-II s-Is in the hexasaccharide fraction of the oligosaccharide mixture. In some embodiments, this fraction ΔIIa-IIs-Is is present in the hexasaccharide fraction to a proportion of from 25% to 50%. The hexasaccharide ΔIIa-IIs-Is contained in the oligosaccharide mixture is a sequence with high affinity for ATIII.

The oligosaccharide mixtures of the present invention may be used as antithrombotic agents. In particular, they are useful for treating or preventing venous and arterial thrombosis, deep vein thrombosis, pulmonary embolism, unstable angina, myocardial infarction, cardiac ischemia, occlusive diseases of the peripheral arteries and atrial fibrillation. They are also useful in preventing and treating smooth muscle cell proliferation, atherosclerosis and arteriosclerosis, for treating and preventing cancer by modulating angiogenesis and growth factors, and for treating and preventing diabetic disorders such as diabetic retinopathy and diabetic nephropathy.

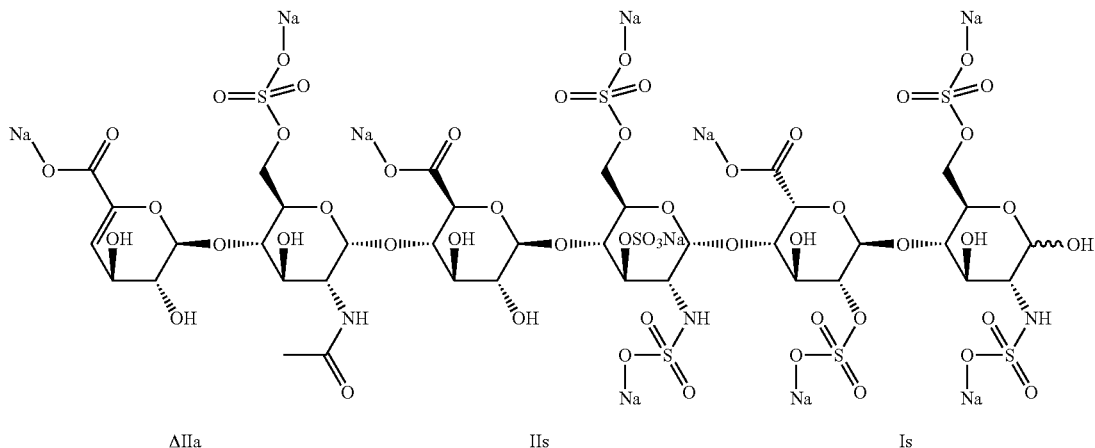

in the form of at least one metal salt chosen from alkali metal and alkaline-earth metal salts.

In some embodiments, the oligosaccharide mixture has an average molecular weight of from 1800 Daltons to 2400 Daltons. In some embodiments, the oligosaccharide mixture has an average molecular weight of from 1900 to 2200 Daltons. In some embodiments, the oligosaccharide mixture has an average molecular weight of from 1950 to 2150 Daltons. In some embodiments, the mixture has an average molecular weight of 2000 Daltons.

In some embodiments, the oligosaccharide mixture has an anti-Xa activity of from 190 IU/mg to 450 IU/mg. In some embodiments, the oligosaccharide mixture has an anti-Xa activity of from 190 IU/mg to 410 IU/mg. In some embodi- Pharmaceutical compositions comprising the purified heparin esters and/or mixtures of sulfated polysaccharides of the invention may be formulated as pharmaceutical mixtures, in which case the composition is substantially dry, or as pharmaceutical solutions or suspensions. The pharmaceutical mixtures, solutions, or suspensions may contain pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the pharmaceutical compositions may be achieved in various ways, including subcutaneous, oral, buccal, rectal, parenteral, intraperitoneal, intradermal, transdermal, intracheal, percutaneous, etc., administration. In the pharmaceutical compositions the purified heparin esters and/ or mixtures of sulfated polysaccharides may be in the form of at least one metal salt chosen from alkali metal and alkaline-earth metal salts.

For oral preparations, the pharmaceutical compositions may comprise one or more appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The pharmaceutical compositions may be formulated into preparations for injection by dissolving, suspending or emulsifying them in an aqueous or nonaqueous solvent, such as water, vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical compositions may also comprise pharmaceutically acceptable excipients, such as vehicles, adjuvants, carriers or diluents, which are known in the art. Moreover, pharmaceutically acceptable auxiliary substances, such as pH adjusting and buffering agents, tonicity adjusting agents, stabilizers, wetting agents and the like, which are known in the art, may be incorporated into the pharmaceutical compositions.

The pharmaceutical compositions of the invention may, for example, be formulated as solutions for subcutaneous or intravenous injection. Other pharmaceutical compositions according to the invention may be formulated for pulmonary administration (inhalation) or oral administration.

The dosage may vary as a function of the age, weight and state of health of the patient. For an adult, it may generally be from 20 to 100 mg per day via the intramuscular or subcutaneous route. The pharmaceutical compositions are, for example, solutions for subcutaneous or intravenous injection. Other pharmaceutical compositions according to the invention are also used for pulmonary administration (inhalation) or oral administration.

In another aspect, the invention provides an oligosaccharide mixture prepared by a process of the invention.

In another aspect, the invention provides a pharmaceutical composition comprising an oligosaccharide mixture of the invention, and a pharmaceutically acceptable carrier. In embodiments, the pharmaceutical composition may be formulated as a solution for subcutaneous or intravenous injection. In other embodiments the pharmaceutical composition may be formulated for pulmonary inhalation. In other embodiments, the pharmaceutical composition may be formulated for oral administration.

In another aspect, the invention provides a method of treating and/or preventing one or more of venous thrombosis, arterial thrombosis, deep vein thrombosis, pulmonary embolism, unstable angina, myocardial infarction, cardiac ischemia, occlusive diseases of the peripheral arteries and atrial fibrillation, smooth muscle cell proliferation, atherosclerosis, arteriosclerosis, cancer by modulating angiogenesis and growth factors, and also diabetic disorders such as diabetic retinopathy or diabetic nephropathy in a patient, the method comprising administering to a patient in need thereof a therapeutically effective amount of an oligosaccharide mixture of the invention.

In another embodiment, the invention provides a method for preventing thrombotic episodes in a patient, comprising administering to a patient in need thereof a therapeutically effective amount of an oligosaccharide mixture of the invention. In another embodiment, the invention provides a method for treating thrombotic episodes in a patient, comprising administering to a patient in need thereof a therapeutically effective amount of an oligosaccharide mixture of the invention. In another embodiment, the invention provides a method for preventing venous thrombosis is a postoperative human patient, comprising administering to a patient in need thereof a therapeutically effective amount of an oligosaccharide mixture of the invention. In another embodiment, the invention provides a method for treating venous thrombosis is a postoperative human patient, comprising administering to a patient in need thereof a therapeutically effective amount of an oligosaccharide mixture of the invention. In another embodiment, the invention provides a therapeutic method for controlling thrombosis and/or decreasing blood hypercoagulation and/or hemorrhaging risks in a human patient, comprising administering to a patient in need thereof a therapeutically effective amount of an oligosaccharide mixture of the invention.

In another aspect the invention provides an article of manufacture for use in connection with the treatment and/or prevention of venous thrombosis, arterial thrombosis, deep vein thrombosis, pulmonary embolism, unstable angina, myocardial infarction, cardiac ischemia, occlusive diseases of the peripheral arteries and atrial fibrillation, smooth muscle cell proliferation, atherosclerosis, arteriosclerosis, cancer by modulating angiogenesis and growth factors, and also diabetic disorders such as diabetic retinopathy or diabetic nephropathy in a patient, comprising an oligosaccharide mixture of the invention, and instructions for the administration thereof.

In another embodiment, the invention provides an article of manufacture for use in connection with the prevention of thrombotic episodes in a patient, comprising an oligosaccharide mixture of the invention and instructions for the administration thereof. In another embodiment, the invention provides an article of manufacture for use in connection with the treatment of thrombotic episodes in a patient, comprising an oligosaccharide mixture of the invention and instructions for the administration thereof. In another embodiment, the invention provides an article of manufacture for use in connection with the prevention of venous thrombosis is a postoperative human patient, comprising an oligosaccharide mixture of the invention and instructions for the administration thereof. In another embodiment, the invention provides an article of manufacture for use in connection with the treatment of venous thrombosis is a postoperative human patient, comprising an oligosaccharide mixture of the invention and instructions for the administration thereof. In another embodiment, the invention provides an article of manufacture for use in connection with controlling thrombosis and/or decreasing blood hypercoagulation and/or hemorrhaging risks in a human patient, comprising an oligosaccharide mixture of the invention and instructions for the administration thereof.

It will be readily apparent to one of ordinary skill in the relevant arts that other suitable modifications and adaptations to the methods and applications described herein are suitable and may be made without departing from the scope of the invention or any embodiment thereof. The following examples are included herewith for purposes of illustration only and are not intended to be limiting of the invention.

Preparation 1: Production of a Starting Low Molecular Weight Heparin

The low molecular weight heparin (LMWH) used as starting material for example 1 was prepared according to patent application WO 2004/033503 from sodium heparin as described above, the depolymerization step being performed in the presence of 2-tert-butylimino-2-diethylamino-1,3-dimethylperhydro-1,3,2-diazaphosphorine in the presence of a percentage of water of less than 0.6%.

The characteristics of the depolymerized heparin thus obtained were as follows:
Average molecular weight: 2400 Daltons
Anti-Xa activity: 158.8 IU/mg
Anti-IIa activity: 3.1 IU/mg
Anti-Xa activity/anti-IIa activity ratio: 51:1

Preparation 2: Production of a Starting Low Molecular Weight Heparin

The low molecular weight heparin (LMWH) used as starting material for examples 2, 3, 4, and 5 was prepared according to patent application WO 2004/033503, from sodium heparin as described above, the depolymerization step being performed in the presence of 2-tert-butylimino-2-diethylamino-1,3-dimethylperhydro-1,3,2-diazaphosphorine in the presence of a percentage of water of less than 0.6%.

The characteristics of the depolymerized heparin thus obtained were as follows:
Average molecular weight: 2450 Daltons
Anti-Xa activity: 158 IU/mg
Anti-IIa activity: 2.1 IU/mg
Anti-Xa activity/anti-IIa activity ratio: 75:1

Preparation 3: LMWH, Benzethonium Salt 12.53 g (20.7 mmol) of the LMWH sodium salt obtained according to preparation 1 were placed in a 500 ml conical flask A and dissolved in 85 ml of water. 31.62 g (70.5 mmol) of benzethonium chloride were placed in a 100 ml conical flask B with 250 ml of water.

The content of B was poured into A and the mixture was stirred for about 1 hour at room temperature. The resulting mixture was left to sediment for about 1 hour. The supernatant was discarded and then replaced with the same volume of water (250 ml). The mixture was stirred for about 15 minutes and left to sediment for approximately 30 minutes. The supernatant was discarded and then replaced with the same volume of water (250 ml). The mixture was stirred for about 15 minutes and then filtered. The cake was washed with 3 times 200 ml of water. The wet beige-colored solid was drained by suction and then dried at 80° C. for about 18 hours in an oven under reduced pressure (6 kPa). 35.56 g of LMWH benzethonium salt were obtained. The yield obtained was 89%.

Preparation 4

17.93 g (30.2 mmol) of LMWH sodium salt obtained according to preparation 2 were placed in a 1 l conical flask A and dissolved in 120 ml of water. 45 g (0.1 mol) of benzethonium chloride were placed in a 500 ml conical flask B with 360 ml of water.

The content of B was poured into A and the mixture was stirred for about 1 hour at room temperature. The resulting mixture was left to sediment for about 1 hour. The supernatant was discarded and then replaced with the same volume of water (500 ml). The mixture was stirred for about 15 minutes and left to sediment for approximately 30 minutes. The supernatant was discarded and then replaced with the same volume of water (500 ml). The mixture was stirred for about 15 minutes and then filtered. The cake was washed with 3 times 200 ml of water. The wet beige-colored solid was drained by suction and then dried at 80° C. for about 48 hours in an oven under reduced pressure (6 kPa). 49.5 g of LMWH benzethonium salt were obtained. The yield obtained was 87%.

EXAMPLE 1

35.39 g (18.3 mmol) of LMWH benzethonium salt obtained according to preparation 3 (with a water content of 0.20%) were dissolved in 183.3 g of dry dichloromethane and placed in a 500 ml three-necked flask. 29.5 ml (25.7 mmol) of benzyl chloride were added at a temperature of 30° C. The percent of esterification was 77% after about 23 hours of reaction at 30° C. After cooling to room temperature (22±3° C.), the reaction mixture was poured into 490 ml of a 10% solution of sodium acetate in methanol. The mixture was stirred for about 1 hour and then left to sediment for approximately 1 hour. The supernatant is discarded and then replaced with the same volume of methanol (250 ml). The mixture was stirred for approximately 30 minutes and then left to sediment for about 45 minutes. The supernatant was discarded and then replaced with the same volume of methanol (250 ml). This mixture was left to sediment for about 16 hours. The supernatant was discarded and then replaced with the same volume of methanol (350 ml). The mixture was stirred for about 5 minutes and the suspension was filtered. The cake was washed with twice 50 ml of methanol, drained by suction and then dried at 40° C. under reduced pressure (6 kPa) for about 18 hours. 34.48 g of crude LMWH benzyl ester sodium salt with a percent esterification of 77% were obtained.

The 34.48 g of crude LMWH benzyl ester sodium salt were dissolved in 350 ml of aqueous 10% NaCl solution. The solution was poured into 1.57 l of methanol. The suspension was stirred for about 40 minutes and was then left to sediment for about 16 hours. The supernatant was discarded and replaced with the same volume of methanol (1.5 l). This mixture was stirred for about 1 hour and was left to sediment for about 1.5 hours. The supernatant was discarded and replaced with the same volume of methanol (1.2 l). This mixture was stirred for approximately 15 minutes and then filtered. The cake was washed with 3 times 50 ml of methanol. The wet white solid was drained by suction and then dried at 40° C. under reduced pressure (6 kPa) for about 18 hours. 6.07 g of LMWH benzyl ester sodium salt were obtained. The esterification yield was 50%.

6 g (9.14 mmol) of LMWH benzyl ester sodium salt were dissolved in 40 ml of water in a 250 ml conical flask A. In parallel, 13.93 g (31 mmol) of benzethonium chloride were placed in 110 ml of water in a 250 ml conical flask B.

The content of B was poured into A. The suspension was stirred for about 1 hour at room temperature (22±3° C.) and then left to sediment for 1 hour. The supernatant was discarded and replaced with the same volume of water (140 ml). This mixture was stirred for about 15 minutes and left to sediment for 1 hour. The supernatant was discarded and replaced with the same volume of water (140 ml). This mixture was stirred for approximately 15 minutes and left to sediment for about 30 minutes. The supernatant was discarded and replaced with the same volume of water (140 ml). This mixture was stirred for about 5 minutes and then filtered. The cake was washed with 3 times 50 ml of water, drained by suction and then dried at 80° C. under reduced pressure (6 kPa) for about 18 hours. 17.43 g of LMWH benzyl ester, benzethonium salt were obtained. The yield was 100%.

17.43 g (9.14 mmol) of LMWH according to preparation 2 were placed in a 250 ml three-necked flask with 122 ml of dry dichloromethane. 17.4 g of 4 Å molecular sieves were added. The mixture was stirred for about 18 hours at room temperature (22±3° C.) under an argon atmosphere.

The sieves were separated from the mixture by transferring the solution into a 250 ml three-necked flask. 2.64 ml (9.14 mmol) of 2-tert-butylimino-2-diethylamino-1,3-dimethylperhydro-1,3,2-diazophosphorine were added and the mixture was stirred for 24 hours at 22±3° C. under an argon atmosphere.

In parallel, 730 ml of methanolic 10% sodium acetate solution were prepared in a 2 l conical flask. 8.71 g of Hyflo supercel Celite were added to the solution. The reaction mixture was poured into the methanolic solution, while maintaining the temperature at about 4° C. The suspension was stirred for about 15 minutes at this temperature. The mixture was left to sediment for approximately 45 minutes at room temperature and the supernatant was then discarded and replaced with the same amount of methanol (450 ml). This mixture was stirred for 15 minutes and left to sediment for approximately 45 minutes. The supernatant was again discarded and replaced with the same amount of methanol (420 ml). This mixture was stirred for about 15 minutes and then filtered through a No. 3 sinter funnel. The cake was washed with twice 70 ml of methanol, drained by suction and then dried for about 18 hours at 50° C. under reduced pressure (6 kPa). 4.35 g of crude depolymerized LMWH (sodium salt) in Celite (8.71 g) were obtained. The yield was 72.5%.

4.35 g (6.63 mmol) of crude depolymerized LMWH (sodium salt) in Celite were dissolved in 46 ml of water and then filtered through a No. 3 sinter funnel. The Celite was rinsed with 2 portions of 30 ml of water. The filtrate was placed in a 500 ml conical flask. 823 µl (9.94 mmol) of 35% sodium hydroxide solution were introduced at a temperature in the region of 4° C. This mixture was stirred for about 3 hours at this temperature. The medium was neutralized by adding 1N HCl solution, followed by addition of 11.5 g of NaCl and 80 ml of methanol. After stirring for approximately 15 minutes, 210 ml of methanol were added. The suspension was stirred for about 1 hour and then left to sediment for 30 minutes. The supernatant was discarded and replaced with the same amount of methanol (230 ml). This mixture was stirred for about 15 minutes and left to sediment for 30 minutes. The supernatant was discarded and replaced with the same amount of methanol (210 ml). This mixture was stirred for approximately 15 minutes and then filtered. The cake was washed with twice 9 ml of methanol, drained by suction and then dried for about 18 hours at 50° C. under reduced pressure (6 kPa). 2.95 g of crude depolymerized LMWH (sodium salt) were obtained. The yield was 73.7%.

1.5 g of crude depolymerized LMWH, sodium salt, were placed in a 50 ml three-necked flask with 16 ml of water. The solution was maintained at 40° C. for about 10 minutes. The pH was brought to about 9.7 by addition of 0.1N sodium hydroxide solution. The solution was filtered through a 0.45 µm membrane, and 84 µl of aqueous 30% hydrogen peroxide solution were then added. The mixture was stirred for 2 hours at room temperature, while keeping the pH constant at 9.7±0.1 by adding 0.1N sodium hydroxide solution. The reaction mixture was then neutralized with 0.1N HCl, and 2 g of NaCl were then added. After stirring for about 10 minutes, the solution was filtered through a 0.45 µm membrane. 14 ml of methanol were added at a temperature in the region of 4° C. The solution was stirred for approximately 15 minutes at room temperature. 36 ml of methanol were then added and the suspension was stirred for about 1 hour. The stirring was then stopped and the mixture was left to sediment for about 30 minutes. The supernatant was then taken up and discarded (40 ml). 40 ml of methanol were added to the sedimented precipitate and this mixture was stirred for about 10 minutes. The precipitate was left to resediment for approximately 30 minutes. The supernatant was taken up and discarded (45 ml). 45 ml of methanol were added and the precipitate in suspension was then filtered off. The white cake obtained was then washed with 2 portions of 3 ml of methanol. The wet solid was drained by suction and then dried under reduced pressure (6 kPa) at a temperature in the region of 50° C. After drying for about 18 hours, 1.303 g of pure depolymerized LMWH (sodium salt) were obtained. The yield obtained was 86.8%.

Characteristics of the depolymerized LMWH thus obtained
Average molecular weight: 1950 Daltons
Polydispersity index: 1.1
Anti-Xa activity: 283 U/mg
anti-IIa activity: undetectable (<0.2 U/mg)

EXAMPLE 2

13.29 g (7.6 mmol) of LMWH benzethonium salt obtained according to preparation 4 were dissolved in 70.43 g of anhydrous dichloromethane and placed in a 100 ml three-necked flask (the water content of the reaction medium was 0.073%). 12.3 ml (107 mmol) of benzyl chloride were added at a temperature of 30° C. The percent esterification was 49% after reaction for about 7 hours at 30° C. After cooling, the reaction mixture was poured into 160 ml of a 12% solution of sodium acetate in methanol. The mixture was stirred for 1 hour at room temperature and then left to sediment for about 16 hours. The supernatant was discarded and then replaced with the same volume of methanol (100 ml). This mixture was stirred for about 1 hour and left to sediment for about 1 hour. The supernatant was again discarded and replaced with the same volume of methanol (100 ml). This mixture was stirred for about 5 minutes and then filtered. The cake was washed with 2×40 ml of methanol, drained by suction and then dried in an oven at 40° C. under reduced pressure (6 kPa) for about 18 hours. 3.90 g of crude LMWH benzyl ester sodium salt with a percent esterification of 49% were obtained.

3.90 g of crude LMWH benzyl ester sodium salt were dissolved in 39 ml of aqueous 10% NaCl solution. The solution was poured into 176 ml of methanol. The suspension was stirred for about 15 minutes and then left to sediment for 2 hours. The mixture was filtered. The cake was resuspended in 175 ml of methanol and stirred for 10 minutes. The mixture was filtered and the cake was washed with 2 portions of 10 ml of methanol. The wet white solid was drained by suction and dried in an oven at 40° C. under reduced pressure (6 kPa) for about 18 hours. 2.62 g of LMWH benzyl ester sodium salt were obtained. The overall yield for the esterification phase was 57.3%.

2.62 g (4.37 mmol) of LMWH benzyl ester sodium salt were dissolved in 20 ml of water (conical flask "A"). In parallel, 5.92 g (13.2 mmol) of benzethonium chloride were placed in 60 ml of water in a conical flask "B".

The content of "B" was poured into "A". The suspension was stirred for about 1 hour at room temperature and then left to sediment for 1 hour. The supernatant was discarded and replaced with the same volume of water (70 ml). This mixture was stirred for about 15 minutes and left to sediment for 1 hour. The supernatant was discarded and replaced with the same volume of water (70 ml). This mixture was stirred for a further 5 minutes approximately and filtered. The cake was washed with 3 portions of 50 ml of water, drained by suction and then dried in an oven at 80° C. under reduced pressure (6 kPa) for about 18 hours. 6.85 g of LMWH benzyl ester benzethonium salt were obtained. The yield was 99%. The water content of the benzethonium salt was 0.6%.

6.80 g (4.3 mmol) of LMWH were placed in a 100 ml three-necked flask with 54 ml of dry dichloromethane. The mixture was brought to 30° C. and then stirred until dissolution was complete. The estimated water content of the reaction mixture was about 0.05%. 1.25 ml (4.3 mmol) of 2-tert-butylimino-2-diethylamino-1,3-dimethylperhydro-1,3,2-diazaphosphorine were added and the mixture was stirred for 24 hours at 30° C. under an inert atmosphere.

In parallel, 270 ml of methanolic 10% sodium acetate solution were prepared in a 1 l conical flask. The reaction mixture was poured into the methanolic solution, while maintaining the temperature at about 4° C. The suspension was stirred for about 1 hour at room temperature. This mixture was left to sediment for 1 hour. The supernatant was discarded and then replaced with the same amount of methanol (165 ml). This mixture was stirred for about 1 hour and left to sediment for 1 hour. The supernatant was again discarded and replaced with the same amount of methanol (170 ml). This mixture was stirred for about 15 minutes and filtered. The cake was washed with 3 portions of 40 ml of methanol, drained by suction and then dried for about 18 hours in an oven at 50° C. under reduced pressure (6 kPa). 2.29 g of crude depolymerized LMWH, sodium salt, were obtained. The yield obtained was 89%.

2.29 g (3.8 mmol) of crude depolymerized LMWH, sodium salt, were dissolved in 23 ml of water. The solution was filtered through a 0.8 μm membrane and then placed in a 100 ml three-necked flask. 575 μl (5.73 mmol) of 30% sodium hydroxide solution were introduced at a temperature in the region of 3° C. The mixture was stirred for about 2 hours at this temperature.

Half of the reaction mixture was neutralized by adding glacial acetic acid, followed by addition of 367 mg of solid sodium acetate and 13 ml of methanol. The solution was stirred for about 15 minutes and 65 ml of methanol were then added. The suspension obtained was stirred for about 30 minutes and was then left to sediment for about 16 hours. The supernatant was discarded and replaced with the same amount of methanol (36 ml). This mixture was stirred for a further 30 minutes approximately and was left to sediment for about 30 minutes. The supernatant was discarded and replaced with the same amount of methanol (16 ml). This mixture was stirred for about 15 minutes and filtered through a 0.22 μm membrane. The cake was washed with twice 5 ml of methanol, drained by suction and then dried under reduced pressure (6 kPa) for about 18 hours in an oven at 50° C. 563 mg of crude depolymerized LMWH (sodium salt) were obtained. The yield was 52.6%.

560 mg of crude depolymerized LMWH (sodium salt) were placed in a 100 ml three-necked flask with 5.6 ml of water. The brown solution was maintained at 40° C. for 10 minutes. The pH was brought to 9.7 by adding 0.1N sodium hydroxide solution. The solution was filtered through a 0.45 μm membrane and 28 μl of aqueous 30% hydrogen peroxide solution were added. The mixture was stirred for 2 hours at room temperature, while keeping the pH constant at 9.5±0.1 by adding 0.1N sodium hydroxide solution. The reaction mixture was neutralized with 0.1N HCl and 620 mg of NaCl were added. After stirring for 10 minutes, the solution was filtered through a 0.45 μm membrane. 4.35 ml of methanol were added at a temperature in the region of 4° C. The solution was stirred for 15 minutes at room temperature. 11.2 ml of methanol were added. The suspension was stirred for 1 hour. The stirring was then stopped and the mixture was left to sediment for 1 hour. The supernatant was then taken up and discarded (13.5 ml). 13.5 ml of methanol were added to the sedimented precipitate and the mixture was stirred for 15 minutes. The precipitate was left to resediment for about 30 minutes. The supernatant was taken up and discarded (13 ml). 13 ml of methanol were added and the precipitate in suspension was then filtered off. The white cake obtained was then washed with 2 portions of 5 ml of methanol. The wet solid was drained by suction and then dried under reduced pressure (6 kPa) at a temperature in the region of 50° C. After drying for 18 hours, 376 mg of pure depolymerized LMWH (sodium salt) were obtained. The yield obtained was 67%.

Characteristics of the depolymerized LMWH thus obtained
Anti-Xa activity: 191 IU/mg
Anti-IIa activity: undetectable (<0.2 U/mg)
Average molecular weight: 2100 Da

EXAMPLE 3

13.7 g (7.3 mmol) of LMWH benzethonium salt obtained according to preparation 4 were dissolved in 73.67 g of anhydrous dichloromethane and placed in a 100 ml three-necked flask (the water content of the reaction medium was assayed as 0.23%). 13 ml (113 mmol) of benzyl chloride were added at a temperature of 30° C. The percent esterification was 73% after reaction for about 20 hours at 30° C. After cooling to room temperature, the reaction mixture was poured into 210 ml of a 12% solution of sodium acetate in methanol. The mixture was stirred for 30 minutes at room temperature and then left to sediment for about 1.5 hours. The supernatant was discarded and then replaced with the same volume of methanol (140 ml). This mixture was stirred for 15 minutes and the suspension was filtered. The cake was washed with 2 portions of 100 ml of methanol, drained by suction and then dried for approximately 18 hours in an oven at 40° C. under reduced pressure (6 kPa). 13.3 g of crude LMWH benzyl ester sodium salt, with a percent esterification of 73%, were obtained.

The 13.3 g of crude LMWH benzyl ester sodium salt were dissolved in 133 ml of aqueous 10% NaCl solution. The solution was poured into 600 ml of methanol. The suspension was stirred for about 15 minutes and then left to sediment for approximately 1 hour. The supernatant was discarded and then replaced with the same volume of methanol (400 ml). This mixture was stirred for about 5 minutes and then filtered. The cake was washed with 3 times 100 ml of methanol. The wet white solid was drained by suction and then dried for approximately 18 hours in an oven at 40° C. under reduced pressure (6 kPa). 2.33 g of LMWH benzyl ester sodium salt were obtained. The esterification yield was 49.6%.

2.27 g (3.53 mmol) of LMWH benzyl ester sodium salt were dissolved in 15 ml of water in a 100 ml conical flask "A". In parallel, 5.22 g (11.6 mmol) of benzethonium chloride were placed in 55 ml of water in a 100 ml conical flask "B". The content of "B" was poured into "A". The suspension was stirred for about 1 hour at room temperature and then left to sediment for approximately 1 hour. The supernatant was discarded and replaced with the same volume of water (50 ml). The mixture was stirred for about 15 minutes and left to sediment for approximately 1 hour. The supernatant was discarded and replaced with the same volume of water (50 ml). The mixture was stirred for a further 5 minutes and then filtered. The cake was washed with 3 portions of 50 ml of water, drained by suction and then dried for about 18 hours in an oven at 80° C. under reduced pressure (6 kPa). 5.67 g of LMWH benzyl ester benzethonium salt were obtained. The yield obtained was 98%. The water content of the product obtained was 1%.

5.45 g (3.3 mmol) of LMWH were placed in a 100 ml three-necked flask with 40 ml of dry dichloromethane. The estimated water content of the mixture was about 0.1%. The mixture was brought to 30° C. 958 µl (3.3 mmol) of 2-tert-butylimino-2-diethylamino-1,3-dimethylperhydro-1,3,2-diazaphosphorine were added and the mixture was stirred for 24 hours at 30° C. under an argon atmosphere.

In parallel, 200 ml of methanolic 10% sodium acetate solution were prepared in a 500 ml conical flask. The reaction mixture was poured into the methanolic solution, while maintaining the temperature at about 4° C. The suspension was stirred for about 1 hour at room temperature. This mixture was left to sediment for approximately 1 hour. The supernatant was discarded and then replaced with the same amount of methanol (150 ml). This mixture was stirred for about 30 minutes and left to sediment for about 30 minutes. The supernatant was again discarded and replaced with the same amount of methanol (150 ml). This mixture was stirred for approximately 15 minutes and then filtered. The cake was washed with 3 times 50 ml of methanol, drained by suction and then dried for about 18 hours at 50° C. under reduced pressure (6 kPa). 1.40 g of crude depolymerized LMWH, sodium salt, were obtained. The yield obtained was 65.8%.

1.40 g (2.18 mmol) of crude depolymerized LMWH (sodium salt) were dissolved in 14 ml of water. The solution was placed in a 100 ml three-necked round-bottomed flask. 351 µl (3.5 mmol) of 30% sodium hydroxide solution were introduced at a temperature in the region of 4° C. This mixture was stirred for about 2 hours at this temperature. The solution was neutralized by adding glacial acetic acid (100%). 7 g of solid sodium acetate and 130 ml of methanol were then added. The suspension was stirred for 30 minutes and was then left to sediment for about 1 hour. The supernatant was discarded and replaced with the same amount of methanol (80 ml). This mixture was stirred for a further 30 minutes approximately and was left to sediment for approximately 16 hours. The supernatant was discarded and replaced with the same amount of methanol (80 ml). This mixture was stirred for about 15 minutes and was then filtered through a 0.45 µm membrane. The cake was washed with twice 10 ml of methanol, drained by suction and then dried for about 18 hours at 50° C. under reduced pressure (6 kPa). 1.15 g (yield: 89.4%) of crude depolymerized LMWH (sodium salt) were obtained. The yield obtained was 89.4%.

373 mg of crude depolymerized LMWH (sodium salt) were placed in a 10 ml three-necked flask with 3.7 ml of water. The solution was maintained at 40° C. for 10 minutes. The pH was brought to about 9.5 by adding 1N sodium hydroxide solution. The solution was filtered through a 0.45 µm membrane and 18 µl of aqueous 30% hydrogen peroxide solution were then added. The mixture was stirred for about 2 hours at room temperature, while keeping the pH constant at 9.5±0.1 by adding 0.1N sodium hydroxide solution. The reaction mixture was neutralized with 0.1N HCl and 430 mg of NaCl were then added. After stirring for about 10 minutes, the solution was filtered through a 0.45 µm membrane. 3 ml of methanol were added at a temperature in the region of 4° C. The solution was stirred for 15 minutes at room temperature. 7.7 ml of methanol were then added. The suspension was stirred for about 1 hour. The stirring was then stopped and the mixture was left to sediment for approximately 40 minutes. The supernatant was then taken up and discarded (10 ml). 10 ml of methanol were added to the sedimented precipitate and the mixture was stirred for 15 minutes. The precipitate was left to resediment for about 30 minutes. The supernatant was taken up and discarded (10 ml). 10 ml of methanol were added and the precipitate in suspension was then filtered off on a 0.45 µm membrane. The white cake obtained was washed with 4 portions of 5 ml of methanol. The wet solid was drained by suction and then dried under reduced pressure (6 kPa) at a temperature in the region of 50° C. After drying for about 18 hours, 199 mg of pure depolymerized LMWH (sodium salt) were obtained. The yield obtained was 54%.

Characteristics of the depolymerized LMWH thus obtained

Average molecular weight: 2000 Daltons.
Polydispersity index: 1.1
Anti-Xa activity: 252 IU/mg
Anti-IIa activity: undetectable (<0.2 U/mg)

EXAMPLE 4

14.45 g (7.7 mmol) of LMWH benzethonium salt obtained according to preparation 4 were dissolved in 75.79 g of anhydrous dichloromethane and placed in a 250 ml three-necked flask (the water content of the reaction medium was 0.20%). 12.4 ml (108 mmol) of benzyl chloride were added at a temperature of 30° C. The percent esterification was 96% after reaction for about 26 hours at 30° C. After cooling to room temperature, the reaction mixture was poured into 180 ml of a 12% solution of sodium acetate in methanol. The mixture was stirred for about 30 minutes at room temperature and was then left to sediment for approximately 30 minutes. The supernatant was discarded and then replaced with the same volume of methanol (150 ml). This mixture was stirred for about 15 minutes and then filtered. The cake was washed with 2 portions of 100 ml of methanol, drained by suction and then dried for about 18 hours at 40° C. under reduced pressure (6 kPa). 3.67 g of crude LMWH benzyl ester, sodium salt, with a percent esterification of 96%, were obtained.

The 3.67 g of crude LMWH benzyl ester, sodium salt were dissolved in 37 ml of aqueous 10% NaCl solution (3.7 g of NaCl in 37 ml of water). The solution was poured into 167 ml of methanol. The suspension was stirred for about 15 minutes and was then left to sediment for approximately 1 hour. The supernatant was discarded and replaced with the same volume of methanol (38 ml). This mixture was stirred for about 5 minutes and filtered. The cake was washed with twice 30 ml of methanol. The wet white solid was drained by suction and dried for about 18 hours at 40° C. under reduced pressure (6 kPa). 2.76 g of LMWH benzyl ester, sodium salt were obtained. The esterification yield was 54.4%.

2.83 g (4.29 mmol) of LMWH benzyl ester, sodium salt, were dissolved in 20 ml of water in a 100 ml conical flask "A". In parallel, 6.35 g (14.2 mmol) of benzethonium chloride were placed in 50 ml of water in a 100 ml conical flask "B".

The content of "B" was poured into "A". The suspension was stirred for about 1 hour at room temperature and was then left to sediment for approximately 1 hour. The supernatant was discarded and replaced with the same volume of water (60 ml). This mixture was stirred for about 15 minutes and left to sediment for approximately 1 hour. The supernatant was discarded and replaced with the same volume of water (60 ml). This mixture was stirred for a further 5 minutes and then filtered. The cake was washed with 4 times 50 ml of water, drained by suction and then dried for about 18 hours at 80° C. under reduced pressure (6 kPa). 7.0 g of LMWH benzyl ester, benzethonium salt, were obtained. The observed yield was about 100%. The water content was 0.23%.

3.67 g (2.3 mmol) of LMWH were placed in a 50 ml three-necked round-bottomed flask with 27 ml of dry dichoromethane. The mixture was brought to 30° C. 676 µl (2.3 mmol) of 2-tert-butylimino-2-diethylamino-1,3-dimethylperhydro-1,3,2-diazaphosphorine were added and the mixture was stirred for 24 hours at 30° C.

In parallel, 150 ml of methanolic 10% sodium acetate solution were prepared in a 250 ml conical flask. The reaction mixture was poured into the methanolic solution, while maintaining the temperature at about 4° C. The suspension was stirred for about 1 hour at room temperature. This mixture was left to sediment for approximately 1 hour. The supernatant was discarded and then replaced with the same amount of methanol (100 ml). This mixture was stirred for 30 minutes and left to sediment for 30 minutes. The supernatant was again discarded and replaced with the same amount of methanol (100 ml). This mixture was stirred for 15 minutes and filtered. The cake was washed with 3 times 40 ml of methanol, drained by suction and dried for about 18 hours at 50° C. under reduced pressure (6 kPa). 966 mg of depolymerized LMWH, sodium salt, were obtained. The yield obtained was 64%.

942 mg (1.43 mmol) of depolymerized LMWH sodium salt were dissolved in 9.5 ml of water. The solution was placed in a 100 ml three-necked round-bottomed flask. 236 µl (2.35 mmol) of 30% sodium hydroxide solution were introduced at a temperature in the region of 4° C. This mixture was stirred for about 2 hours at room temperature. The solution was neutralized by addition of glacial acetic acid (100%). 4.5 g of solid sodium acetate and 85 ml of methanol were then added. The suspension was stirred for about 30 minutes and then left to sediment for about 1 hour. The supernatant was discarded and replaced with the same amount of methanol (40 ml). This mixture was stirred for a further 30 minutes approximately and was left to sediment for about 16 hours. The supernatant was discarded and replaced with the same amount of methanol (40 ml). This mixture was stirred for about 30 minutes and filtered through a 0.45 µm membrane. The cake was washed with twice 10 ml of methanol, drained by suction and then dried for about 18 hours at 50° C. under reduced pressure (6 kPa). 776 mg of crude depolymerized LMWH (sodium salt) were obtained. The yield obtained was 91.4%.

758 mg of crude depolymerized LMWH (sodium salt) were placed in a 25 ml three-necked flask with 7.6 ml of water. The solution was maintained at 40° C. for 10 minutes. The pH was brought to about 9.5 by addition of 0.1N sodium hydroxide solution. The solution was filtered through a 0.45 µm membrane, and 38 µl of aqueous 30% hydrogen peroxide solution were then added. The mixture was stirred for about 2 hours at room temperature, while keeping the pH constant at 9.5±0.1 by addition of 0.1N sodium hydroxide solution. The reaction mixture was neutralized with 1N HCl and 880 mg of NaCl were added. After stirring for about 10 minutes, the solution was filtered through a 0.45 µm membrane. 6.2 ml of methanol were added at a temperature in the region of 4° C. The solution was stirred for approximately 15 minutes at room temperature. 16 ml of methanol were added and the suspension was stirred for about 1 hour. The stirring was then stopped and the suspension was filtered. The cake was washed with 2 portions of 15 ml of methanol. The wet solid was drained by suction and then dried under reduced pressure (6 kPa) at a temperature in the region of 50° C. After drying for approximately 18 hours, 490 mg of pure depolymerized LMWH (sodium salt) were obtained. The yield obtained was 65%.

Characteristics of the depolymerized LMWH thus obtained
Average molecular weight: 2000 Daltons
Polydispersity index: 1.1
Anti-Xa activity: 205 IU/mg
Anti-IIa activity: undetectable (<0.2 U/mg)

EXAMPLE 5

3.67 g (2.3 mmol) of LMWH benzyl ester, benzethonium salt, obtained according to example 4 (96% esterified), with a water content of 0.23%, were placed in a 50 ml three-necked flask with 30 ml of dry dichloromethane. The mixture was brought to 30° C. 595 µl (2.3 mmol) of tert-butyliminotris (dimethylamino)phosphorane were added and the mixture was stirred for 24 hours at 30° C.

In parallel, 160 ml of methanolic 10% sodium acetate solution were prepared in a 250 ml conical flask. The reaction mixture was poured into the methanolic solution, while maintaining the temperature at about 4° C. The suspension was stirred for approximately 1 hour at room temperature. This mixture was left to sediment for about 1 hour. The supernatant was discarded and then replaced with the same amount of methanol (120 ml). This mixture was stirred for about 30 minutes and left to sediment for 30 minutes. The supernatant was again discarded and replaced with the same amount of methanol (125 ml). This mixture was stirred for about 15 minutes and filtered. The cake was washed with 3 times 40 ml of methanol, drained by suction and dried for about 18 hours at a temperature in the region of 50° C. under reduced pressure (6 kPa). 982 mg of crude depolymerized LMWH, sodium salt, were obtained. The yield obtained was 65%.

980 mg (1.49 mmol) of crude depolymerized LMWH, sodium salt, were dissolved in 10 ml of water. The solution was placed in a 100 ml three-necked round-bottomed flask. 246 µl (2.45 mmol) of 30% sodium hydroxide solution were introduced at a temperature in the region of 4° C. This mixture was stirred for about 2 hours at this temperature. The solution was neutralized by adding glacial acetic acid (100%). 4.9 g of solid sodium acetate and 95 ml of methanol were then added. The suspension was stirred for 30 minutes and then left to sediment for about 1 hour. The supernatant was discarded and then replaced with the same amount of methanol (60 ml). This mixture was stirred for a further 30 minutes approximately and was then left to sediment for about 16 hours. The supernatant was discarded and then replaced with the same amount of methanol (60 ml). This mixture was stirred for about 30 minutes and filtered through a 0.45 µm membrane. The cake was washed with twice 10 ml of methanol, drained by suction and then dried for approximately 18 hours at 50° C. under reduced pressure (6 kPa). 809 mg of crude depolymerized LMWH, sodium salt, were obtained. The reaction yield was 91.6%.

792 mg of crude depolymerized LMWH (sodium salt) were placed in a 25 ml three-necked flask with 8 ml of water. The solution was maintained at 40° C. for 10 minutes. The pH was brought to about 9.5 by adding 0.1N sodium hydroxide solution. The solution was filtered through a 0.45 µm membrane, and 39.6 µl of aqueous 30% hydrogen peroxide solution were then added. The mixture was stirred for 2 hours at room temperature, while keeping the pH constant at 9.5±0.1 by adding 0.1N sodium hydroxide solution. The reaction mixture was neutralized with 1N HCl and 1.04 g of NaCl were added. After stirring for about 10 minutes, the solution was filtered through a 0.45 µm membrane. 7.3 ml of methanol were added at a temperature in the region of 4° C. The solution was stirred for 15 minutes at room temperature. 18.8 ml of methanol were added and the suspension was stirred for about 1 hour. The stirring was then stopped and the mixture was filtered. The cake was washed with 3 portions of 15 ml of methanol. The wet solid was drained by suction and then dried under reduced pressure (6 kPa) at a temperature in the region of 50° C. After drying for 18 hours, 538 mg of pure depolymerized LMWH (sodium salt) were obtained. The yield obtained was 67.9%.

Characteristics of the depolymerized LMWH thus obtained
Average molecular weight: 2100 Daltons
Polydispersity index: 1.1
Anti-Xa activity: 209 IU/mg
Anti-IIa activity: undetectable (<0.2 U/mg)

EXAMPLE 6

The oligosaccharide mixture described in example 1 (286 mg) was dissolved in 20 ml of mobile phase (aqueous sodium bicarbonate solution at a concentration of 0.2 mol/l). The chromatographic conditions were as follows:
Mobile phase: sodium bicarbonate solution at a concentration of 0.2 mol/l
Stationary phase: biogel P6 gel
Column: length 1 m, diameter 5 cm
Detection wavelength: 240 nm.

The fractions greater than or equal to a hexasaccharide were collected and pooled. They were neutralized with acetic acid and then concentrated until a solution containing 200 g/l of sodium acetate was obtained. 5 volumes of methanol were added to the solution obtained with stirring. The suspension was stirred for about 18 hours and then filtered through a 0.45 µm membrane. The cake was dried for about 6 hours at a temperature in the region of 40° C. under reduced pressure (6 kPa). The product obtained was reprecipitated and then dissolved in a minimum amount of water and desalified on a Sephadex G10 column. After concentrating the desalified fractions and then freeze-drying, 109 mg of product were obtained. The yield was 38%.

The characteristics of the oligosaccharide mixture thus obtained were as follows:
Average molecular weight: 2150 Daltons
Anti-Xa activity: 403 IU/mg
Anti-IIa activity: undetectable (<0.2 U/mg)
The oligosaccharide percentage was as follows:

| Mw (Da) | Poly-dispersity | Di % | Tetra % | Hexa % | Octa % | Deca % | >Deca % |
|---|---|---|---|---|---|---|---|
| 2150 | 1.0 | 0 | 0 | 53.83 | 32.58 | 10.5 | 3.5 |

Percentage of hexasaccharide Δ IIa-IIs-Is in the compounds according to the invention:

| Examples | Percentage of hexasaccharide fraction | Percentage of hexasaccharide Δ IIa-IIs-Is in the hexasaccharide fraction |
|---|---|---|
| 1 | 31% | 46% |
| 2 | 30% | 26% |
| 3 | 33% | 33.5% |
| 4 | 32% | 30.8% |
| 5 | 31.5% | 28.7% |
| 6 | 53.8% | 46% |

While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

What is claimed is:

1. An oligosaccharide mixture, wherein:
the oligosaccharide mixture comprises an anti-Xa activity of from 200 IU/mg to 450 IU/mg;
the oligosaccharide mixture comprises an anti-IIa activity of less than 0.2 UI/mg;
the constituent oligosaccharides of the mixture have an average molecular weight of from 1800 to 2400 Daltons;
the constituent oligosaccharides of the mixture comprise from 2 to 16 saccharide units;
wherein:
from 20% to 100% of the oligosaccharides of the mixture are hexasaccharides;
from 20% to 70% of the hexasaccharides have the sequence:
the constituent oligosaccharides of the mixture comprise oligosaccharides comprising a hexasaccharide of the following formula:

the constituent oligosaccharides of the mixture are in the form of at least one metal salt chosen from alkali metal and alkaline-earth metal salts.

2. The oligosaccharide mixture according to claim 1, wherein the mixture comprises an anti-Xa activity of from 200 IU/mg to 410 IU/mg.

3. The oligosaccharide mixture according to claim 1, wherein the mixture comprises an anti-Xa activity of from 200 IU/mg to 300 IU/mg.

4. The oligosaccharide mixture according to claim 1, wherein the constituent oligosaccharides of the mixture have an average molecular weight of from 1900 to 2200 Daltons.

5. The oligosaccharide mixture according to claim 4, wherein the constituent oligosaccharides of the mixture have an average molecular weight of from 1950 to 2150 Daltons.

6. The oligosaccharide mixture according to claim 5, wherein the constituent oligosaccharides of the mixture have an average molecular weight of 2000 Daltons.

7. The oligosaccharide mixture according to claim 1, wherein from 25% to 50% of the hexasaccharides have the sequence:

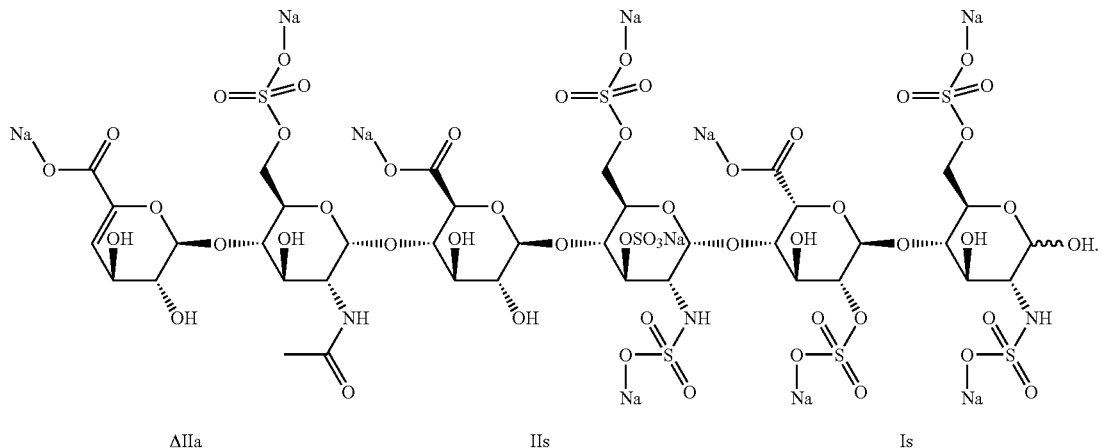

8. The oligosaccharide mixture according to claim 1, wherein from 20% to 70% of the oligosaccharides of the mixture are hexasaccharides.

9. The oligosaccharide mixture according to claim 8, wherein from 20% to 70% of the hexasaccharide fraction in the oligosaccharide mixture has the sequence:

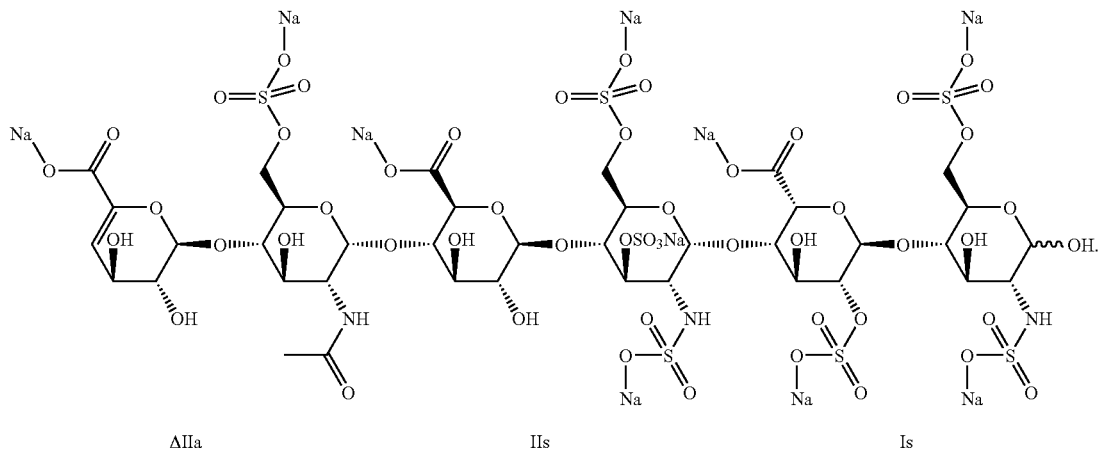

10. The oligosaccharide mixture according to claim 8, wherein from 25% to 50% of the hexasaccharides have the sequence:

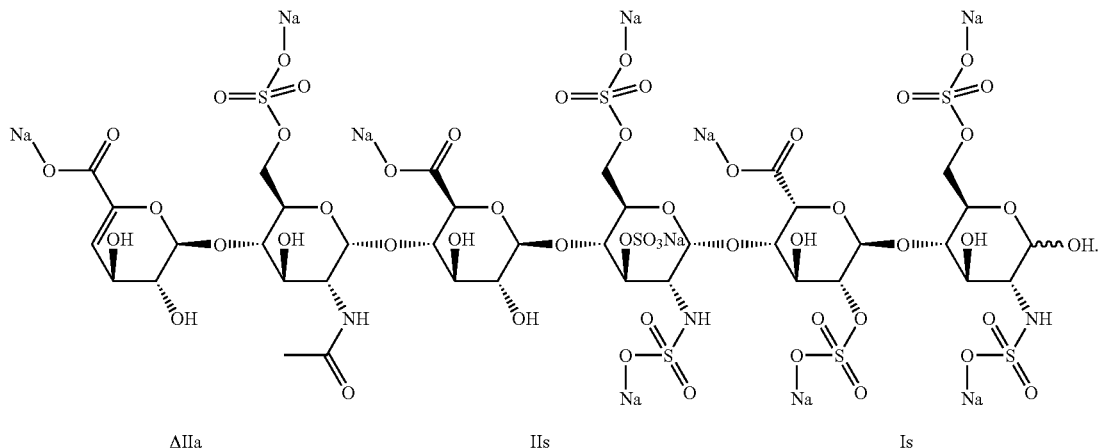

ΔIIa    IIs    Is

11. The oligosaccharide mixture according to claim 1, wherein the at least one metal salt is chosen from sodium, potassium, calcium and magnesium salts.

12. The oligosaccharide mixture of claim 1, wherein the oligosaccharide mixture is obtained directly from depolymerization of a quaternary ammonium salt of a low molecular weight heparin benzyl ester by a strong organic base with a pKa value of greater than 20.

13. A pharmaceutical composition comprising an oligosaccharide mixture according to claim 1, and a pharmaceutically acceptable carrier.

14. The pharmaceutical composition of claim 13, formulated as a solution for subcutaneous or intravenous injection.

15. The pharmaceutical composition of claim 13, formulated for pulmonary inhalation.

16. The pharmaceutical composition of claim 13, formulated for oral administration.

* * * * *